US008206649B2

(12) United States Patent
Suzuki et al.

(10) Patent No.: US 8,206,649 B2
(45) Date of Patent: Jun. 26, 2012

(54) COMPONENT MEASURING APPARATUS

(75) Inventors: Yoshiro Suzuki, Nakakoma-gun (JP); Yasushi Nagasawa, Nakakoma-gun (JP); Eiji Arita, Nakakoma-gun (JP); Masakazu Ishizu, Yao (JP); Yasuhiro Yamamoto, Yao (JP)

(73) Assignees: Terumo Kabushiki Kaisha, Shibuya-Ku, Tokyo (JP); Hosiden Corporation, Yao-Shi, Osaka (JP)

( * ) Notice: Subject to any disclaimer, the term of this patent is extended or adjusted under 35 U.S.C. 154(b) by 136 days.

(21) Appl. No.: 12/521,718

(22) PCT Filed: Jan. 8, 2008

(86) PCT No.: PCT/JP2008/050071
§ 371 (c)(1),
(2), (4) Date: Jun. 29, 2009

(87) PCT Pub. No.: WO2008/087876
PCT Pub. Date: Jul. 24, 2008

(65) Prior Publication Data
US 2010/0317092 A1 Dec. 16, 2010

(30) Foreign Application Priority Data
Jan. 19, 2007 (JP) .................................. 2007-010623

(51) Int. Cl.
*G01N 15/06* (2006.01)
*G01N 33/00* (2006.01)
*G01N 33/48* (2006.01)

(52) U.S. Cl. ......... 422/68.1; 422/60; 422/400; 422/401; 422/402; 422/405; 422/408; 422/410; 422/412; 422/419; 422/82.01; 422/82.02; 422/501; 422/502; 422/524; 436/43; 436/66

(58) Field of Classification Search ............. 422/60, 422/68.1, 400, 401, 402, 405, 408, 410, 412, 422/419, 82.01, 82.02, 501, 502, 524; 436/43, 436/66
See application file for complete search history.

(56) References Cited

U.S. PATENT DOCUMENTS
4,637,403 A * 1/1987 Garcia et al. .................. 600/583
(Continued)

FOREIGN PATENT DOCUMENTS
JP 63-175850 U 11/1988
(Continued)

OTHER PUBLICATIONS
International Search Report (PCT/ISA/210) for PCT/JP2008/050071 dated Mar. 4, 2008.
(Continued)

Primary Examiner — Brian J Sines
(74) Attorney, Agent, or Firm — Buchanan Ingersoll & Rooney PC

(57) ABSTRACT

A component measuring apparatus is provided with a case having a cylindrical case main body and a cover arranged to cover the base end opening section of the case main body; a chip mounting section for mounting a chip; a light measuring section for detecting a prescribed component; a printed board whereupon a control section having a function of controlling the operation of the light measuring section is arranged; a liquid crystal display device; a battery arranging section for arranging a battery provided on the cover; an O-ring arranged between the case main body and the light measuring section on the leading end section of the case main body; and an O-ring arranged between the case main body and the cover on the base end opening section of the case main body. Sealing of inside the case is ensured by the O-ring.

11 Claims, 13 Drawing Sheets

U.S. PATENT DOCUMENTS

| | | | |
|---|---|---|---|
| 5,279,294 A * | 1/1994 | Anderson et al. | 600/322 |
| 5,536,249 A * | 7/1996 | Castellano et al. | 604/65 |
| 5,736,103 A * | 4/1998 | Pugh | 422/68.1 |
| 5,947,957 A * | 9/1999 | Morris | 606/13 |
| 6,009,339 A * | 12/1999 | Bentsen et al. | 600/322 |
| 6,101,406 A * | 8/2000 | Hacker et al. | 600/322 |
| 6,197,040 B1 * | 3/2001 | LeVaughn et al. | 606/182 |
| 6,338,720 B1 | 1/2002 | Morikawa et al. | |
| 7,303,726 B2 * | 12/2007 | McAllister et al. | 422/68.1 |
| 7,586,610 B2 * | 9/2009 | Nagasawa | 356/402 |
| 7,981,056 B2 * | 7/2011 | Briggs et al. | 600/583 |
| 7,988,645 B2 * | 8/2011 | Freeman et al. | 600/583 |
| 2006/0243031 A1 * | 11/2006 | Kondo et al. | 73/53.01 |
| 2009/0105613 A1 * | 4/2009 | Nishiuchi | 600/583 |

FOREIGN PATENT DOCUMENTS

| | | |
|---|---|---|
| JP | 05-072169 A | 3/1993 |
| JP | 09-297120 A | 11/1997 |
| JP | 2000-230904 A | 8/2000 |
| JP | 2000-230905 A | 8/2000 |
| JP | 2004-347436 A | 12/2004 |
| JP | 2005-091315 A | 4/2005 |
| JP | 2006-138774 A | 6/2006 |

OTHER PUBLICATIONS

Written Opinion (PCT/ISA/237) for PCT/JP2008/050071 dated Mar. 4, 2008.

Japanese Office Action dated May 8, 2012 issued in the corresponding Japanese Patent Application No. 2008-554009.

* cited by examiner

COMPONENT MEASURING APPARATUS

TECHNICAL FIELD

The present invention relates to a component measuring apparatus for measuring the quantity and/or quality of a predetermined component in a specimen.

BACKGROUND ART

Various component measuring apparatuses are used to detect a prescribed component in various specimens and measure the quantity and quality of the prescribed component. The component measuring apparatuses are adapted to sample a specimen with a disposable sampling device (tip) and detect a prescribed component in the specimen sampled in the sampling device.

Some specimens contain microorganisms and chemical substances which are harmful to the human body. While such a specimen is being measured by a component measuring apparatus, if a portion of the specimen is adhered to the component measuring apparatus, then an action should be taken to keep the adhered specimen out of direct contact with people other than the specimen donor from the standpoint of safety and hygiene.

For example, Patent document 1 discloses a blood glucose measuring apparatus (blood component measuring apparatus) for measuring a blood glucose level. Although the blood glucose measuring apparatus employs electronic components in various sections thereof, no hermetic sealing is ensured in the apparatus.

Therefore, when the blood glucose measuring apparatus is washed, antisepticized, sterilized, or otherwise processed for cleaning the apparatus, e.g., for removing any blood adhered to the apparatus, the washing fluid, the antisepticizing fluid, the sterilizing gas, or the like enters the blood glucose measuring apparatus, tending to cause the apparatus to suffer a breakdown.

Patent document 1: Japanese Laid-Open Patent Publication No. 2004-347436

DISCLOSURE OF THE INVENTION

It is an object of the present invention to provide a component measuring apparatus which can be washed, antisepticized, or otherwise processed and can be used repeatedly with safety.

To achieve the above object, there is provided in accordance with the present invention a component measuring apparatus for measuring the quantity and/or quality of a predetermined component in a specimen, comprising:

a case including a tubular case body having a distal-end opening, a proximal-end opening, and a window, and a lid disposed so as to cover the proximal-end opening of the case body;

a sampling device mounting part projecting outwardly from a distal end of the case body for detachably mounting thereon a sampling device for sampling the specimen;

a detector for detecting the predetermined component, the detector being disposed in the distal-end opening of the case body and having at least a portion positioned inside the case body;

a controller electrically connected to the detector and including a measuring unit for measuring the predetermined component, the controller having a function to control operation of at least the detector;

a display having a function to display a measurement result measured by the measuring unit, for allowing the measurement result to be visually recognized through the window;

a cell mounting part for mounting a cell for supplying electric power to at least the controller;

first hermetic sealing means disposed in the distal-end opening between the case body and the detector; and second hermetic sealing means disposed in the proximal-end opening between the case body and the lid;

wherein a housing space defined by the case body, the lid, and the detector for housing the controller, the display, and the cell mounting part is hermetically sealed by the first hermetic sealing means and the second hermetic sealing means.

With the above arrangement, the component measuring apparatus can be washed, antisepticized, or otherwise processed and can be used repeatedly with safety.

In the component measuring apparatus according to the present invention, the first hermetic sealing means should preferably comprise a first annular member disposed on an outer circumferential portion of the detector and made of an elastic material.

With this arrangement, reliable hermetic sealing is provided between the case body and the detector by a simple arrangement.

In the component measuring apparatus according to the present invention, the lid should preferably have a fitting portion fitted in the proximal-end opening of the case body, and the second hermetic sealing means should preferably comprise a second annular member disposed on an outer circumferential portion of the fitting portion and made of an elastic material.

With this arrangement, reliable hermetic sealing is provided between the case body and the lid by a simple structure.

The component measuring apparatus according to the present invention should preferably further comprise an inner case housing the controller therein and supporting at least the detector and the display.

With this arrangement, increased hermetic sealing is provided in the component measuring apparatus.

In the component measuring apparatus according to the present invention, the sampling device mounting part should preferably be disposed on a distal end portion of the detector.

With this arrangement, the component measuring apparatus is simplified in structure and reduced in manufacturing cost.

In the component measuring apparatus according to the present invention, the detector should preferably have a portion projecting from the case body through the distal-end opening.

With this arrangement, increased hermetic sealing is provided in the case.

In the component measuring apparatus according to the present invention, the portion of the detector projecting from the case body should preferably have a projection projecting outwardly substantially perpendicularly to an axial direction of the case body, and a fitting member for holding the first hermetic sealing means in increased close contact with the case body and the detector should preferably be fitted between the projection and the distal end of the case body.

With this arrangement, the hermetic sealing forces of the first hermetic sealing means are increased (intensified) to provide more reliable hermetic sealing between the case body and the detector.

In the component measuring apparatus according to the present invention, an ejector member for removing the sampling device mounted on the sampling device mounting part from the sampling device mounting part should preferably be disposed outside of the distal end portion of the case body.

With this arrangement, it is easy to remove the sampling device mounted on the sampling device mounting part.

In the component measuring apparatus according to the present invention, the ejector member should preferably be supported movably along axial directions of the case body.

With this arrangement, the sampling device mounted on the sampling device mounting part can be removed in a simple operation.

In the component measuring apparatus according to the present invention, a distal-end cover member housing therein the ejector member for guiding the ejector member for movement should preferably be disposed on the distal end portion of the case body.

With this arrangement, the ejector member can be moved accurately.

In the component measuring apparatus according to the present invention, the ejector member should preferably have an abutment for abutting against the sampling device, and the distal-end cover member should preferably have a through hole into which the abutment is inserted.

With this arrangement, inasmuch as the sampling device can be pressed by the abutment when the sampling device mounted on the sampling device mounting part is to be removed, the operation (removing operation) can be performed more reliably.

In the component measuring apparatus according to the present invention, the distal-end cover member should preferably have a through hole into which at least the sampling device mounting part is inserted.

With this arrangement, the distal-end cover member can be detached from the case when necessary (e.g., when replacing the ejector member).

The component measuring apparatus according to the present invention should preferably further comprise a switch electrically connected to the controller, wherein the case body should preferably have a through hole into which a portion of the switch is inserted, the through hole being hermetically sealed by an elastic member.

With this arrangement, the through hole can be reliably hermetically sealed to provide reliable hermetic sealing in the component measuring apparatus. The component measuring apparatus can be washed, antisepticized, or otherwise processed and can be used repeatedly with safety.

In the component measuring apparatus according to the present invention, the elastic member should preferably be integrally formed with the case body by multicolor molding.

With this arrangement, the elastic member is prevented from being peeled off the case body, and can hermetically seal the case body reliably for a long period of time.

In the component measuring apparatus according to the present invention, the cell mounting part should preferably be integrally formed with or coupled to the lid.

With this arrangement, the number of parts of the component measuring apparatus is reduced, and the cell can easily be replaced.

In the component measuring apparatus according to the present invention, the case body should preferably have an inspection through hole for inspecting the component measuring apparatus about hermetic sealing therein, the inspection through hole being sealed by a sealing member.

With this arrangement, hermetic sealing is ensured in the case unless necessary (inspection for hermetic sealing).

In the component measuring apparatus according to the present invention, the inspection through hole should prefer-ably be connectable to an inspecting device for inspecting the component measuring apparatus about hermetic sealing therein.

With this arrangement, it is possible to inspect the component measuring apparatus for its level of hermetic sealing (liquid tightness, air tightness).

To achieve the above object, there is provided in accordance with the present invention a component measuring apparatus for measuring the quantity of a predetermined component in a body fluid, comprising:

a case including a tubular case body having a distal-end opening, a proximal-end opening, and a window, and a lid disposed so as to cover the proximal-end opening;

a detector for detecting the predetermined component, the detector being disposed in the distal-end opening of the case body;

a tip mounting part projecting outwardly from the detector for detachably mounting thereon a component measuring tip for sampling the body fluid;

a measuring unit for calculating a value of the predetermined component from a signal detected by the detector;

a display having a function to display the calculated value of the predetermined component, for allowing the displayed value to be visually recognized through the window;

a cell mounting part for mounting a cell serving as a power supply of the component measuring apparatus;

first hermetic sealing means disposed in the distal-end opening between the case body and the detector; and second hermetic sealing means disposed in the proximal-end opening between the case body and the lid;

wherein a housing space defined by the case body, the lid, and the detector for housing the measuring unit, the display, and the cell mounting part is hermetically sealed by the first hermetic sealing means and the second hermetic sealing means.

With the above arrangement, the component measuring apparatus can be washed, antisepticized, or otherwise processed and can be used repeatedly with safety.

BEST MODE FOR CARRYING OUT THE INVENTION

Prior to describing component measuring apparatus according to embodiments of the present invention, an embodiment of a tip (component measuring tip (sampling device)) to be mounted on a component measuring apparatus according to the present invention for use will first be described.

Figure 11:
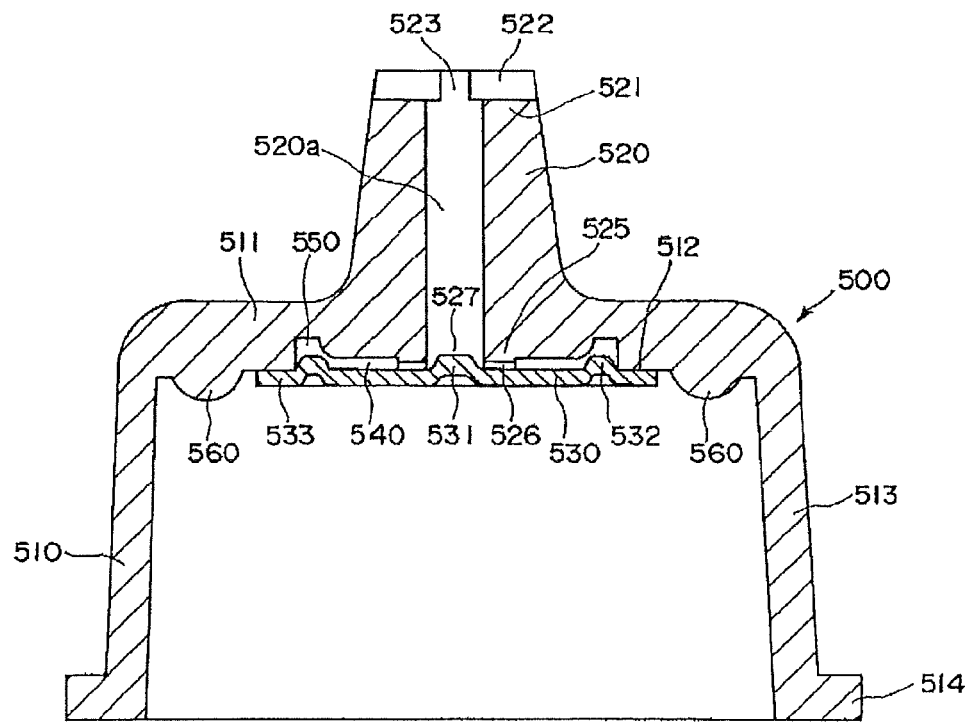
FIG. 11 is a vertical cross-sectional view of a tip.
Figure 12:
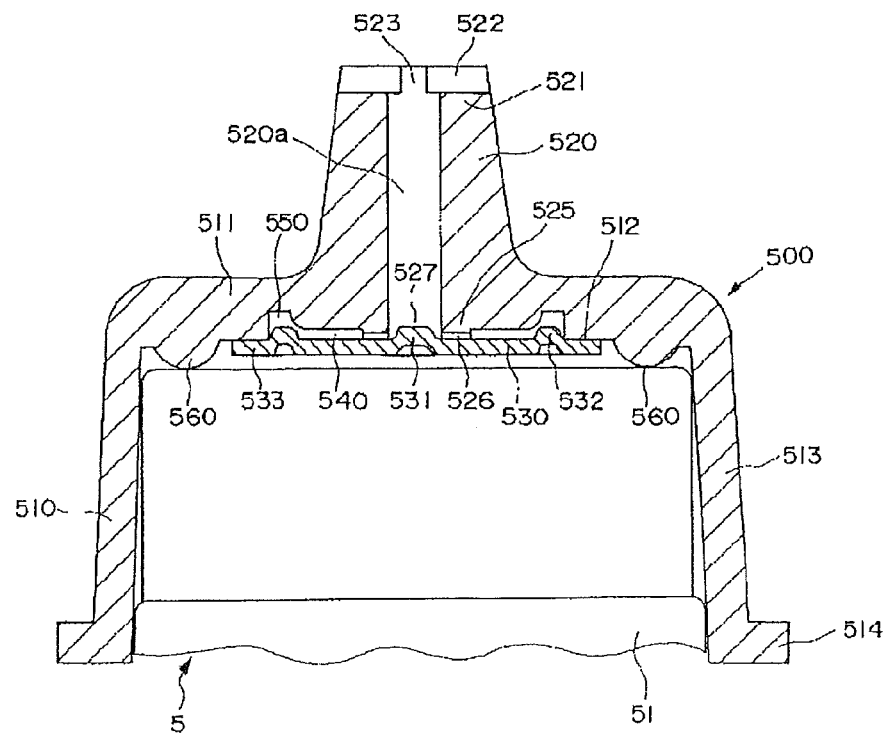
FIG. 12 is a vertical cross-sectional view of the tip shown in FIG. 11 which is mounted on a component measuring apparatus.

FIG. 11 is a vertical cross-sectional view of a tip, and FIG. 12 is a vertical cross-sectional view of the tip shown in FIG. 11 which is mounted on a component measuring apparatus. In FIGS. 11 and 12, a lower side will be described as "proximal end" and an upper side as "distal end".

A tip 500 shown in FIG. 11 comprises a tip body 510 in the form of a bottomed tube, a narrow tube 520 projecting from a bottom 511 of the tip body 510, and a test paper 530 disposed in the tip body 510.

The tip body 510 supports the test paper 530 and forms a mounting part for mounting the tip 500 on a tip mounting part (sampling device mounting part) 5 of a component measuring apparatus 1 to be described later.

The tip body 510 comprises the bottom 511, a barrel 513, and a flange 514 formed on an outer circumferential surface of the proximal end of the barrel 513. A seat 512 for securing the test paper 530 is formed on an inner surface of the bottom 511. The test paper 530 has an outer circumferential portion (fixing portion 533) fixed to the seat 512 by fusion bonding, adhesive bonding, or the like.

Figure 13:
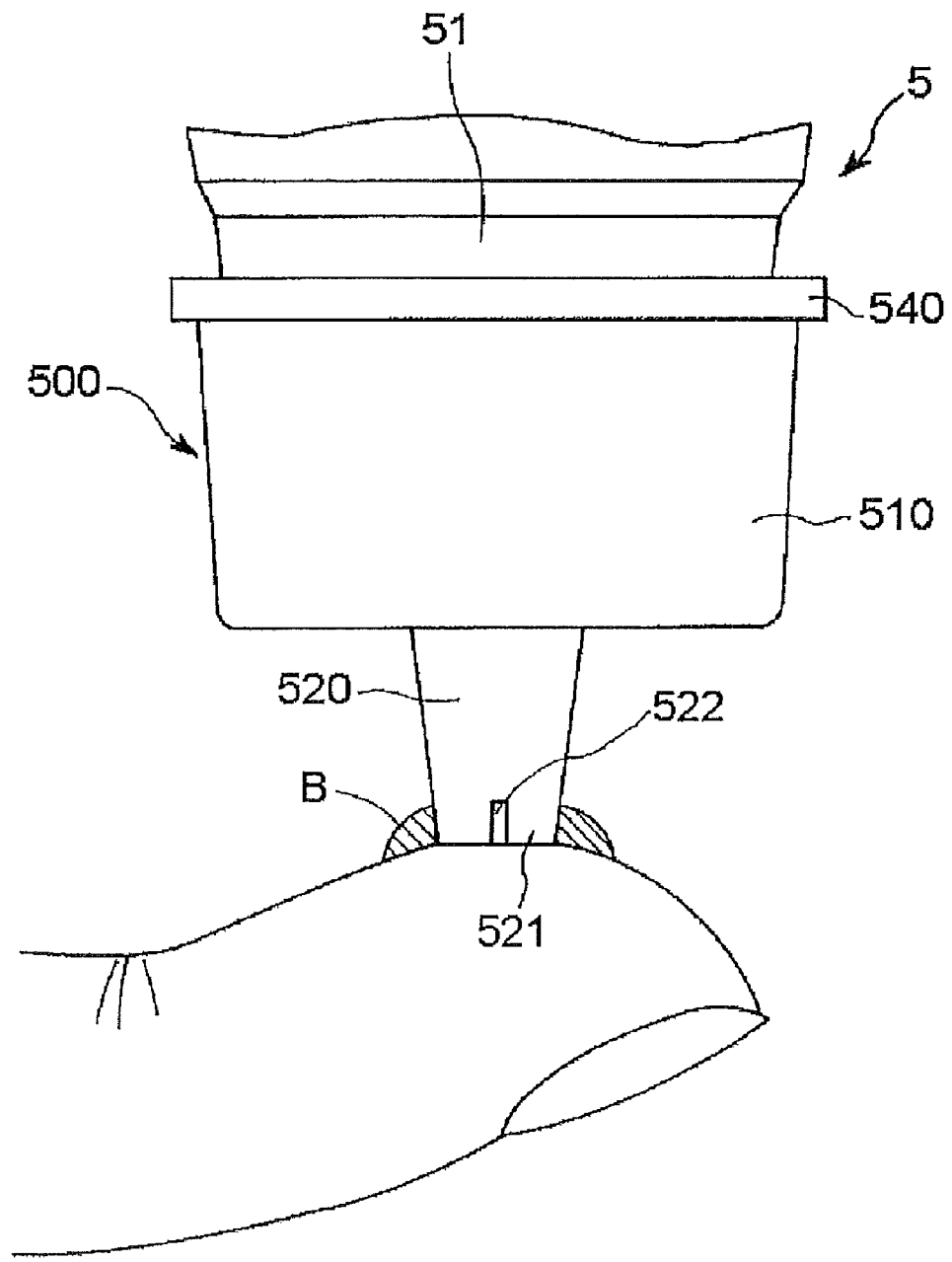
FIG. 13 is a side elevational view showing the manner in which blood is sampled using the tip shown in FIG. 11.

The barrel 513 forms the mounting part for mounting the tip 500 on the tip mounting part 5 of the component measuring apparatus 1. Specifically, as shown in FIGS. 12 and 13, a fitting portion 51 of the tip mounting part 5 is fitted inside the barrel 513 of the tip body 510, mounting the tip 500 on the component measuring apparatus 1. The state shown in FIG. 12 will be hereinafter referred to as a "tip mounted state".

The narrow tube 520 serves to sample blood (specimen) and has a specimen introducing passage 520a formed therein. The specimen introducing passage 520a extends in a direction which is substantially perpendicular to the test paper 530, and has a specimen inlet port 523 in its distal end and a specimen outlet port 527 in its proximal end.

The blood is supplied through the specimen introducing passage 520a to the test paper 530 according to the capillary action. The specimen introducing passage 520a has an inner diameter (transverse cross-sectional area) which may be constant or vary along the longitudinal directions of the specimen introducing passage 520a.

As shown in FIG. 11, the narrow tube 520 has a distal end portion and a proximal end portion which serve respectively as a specimen inlet end portion 521 and a specimen outlet end portion 525.

A groove 522 held in fluid communication with the specimen introducing passage 520a is formed in an end face of the specimen inlet end portion 521. In the illustrated arrangement, the groove 522 comprises a linear groove extending along a diameter direction of the narrow tube 520. The groove 522 has opposite ends which are open at the outer circumferential surface of the narrow tube 520.

The specimen outlet end portion 525 (facing the test paper 530) of the narrow tube 520 forms a protrusion which slightly projects from the bottom 511 in the tip body (toward the proximal end). The specimen outlet end portion 525 has a groove (second groove) 526 formed therein which is held in fluid communication with the specimen introducing passage 520a. In the illustrated arrangement, the groove 526 comprises a linear groove extending along a diameter direction of the narrow tube 520. The groove 526 has opposite ends which are open at the outer circumferential surface of the protrusion.

As shown in FIG. 11, a gap 540 is provided on a side of the test paper 530 closer to the narrow tube 520, i.e., between the test paper 530 and the inner surface of the bottom 511 of the tip body 510. The gap 540 has a function to assist in spreading the blood on the test paper 530.

A specimen pool 550 is provided in an outer circumferential region of the gap 540 and held in fluid communication with the gap 540. The specimen pool 550 comprises an annular recess that is deeper than the gap 540. The blood that is spread radially through the gap 540 pools in the specimen pool 550 and is prevented from moving further radially outwardly (into the portion of the test paper 530 that is fixed by adhesive bonding, fusion bonding, or the like). Therefore, even if the blood is excessively supplied, excessive blood is prevented from leaking out, and a photometric unit 4, etc. of the component measuring apparatus 1 is prevented from being contaminated by blood contact.

The inner surface of the bottom 511 of the tip body 510 has a spacer 560 positioned radially outwardly of the seat 512 and serving as a spacing means for keeping the test paper 530 and the tip mounting part 5 out of contact with each other in the tip mounted state.

The spacer 560 comprises a plurality of bumps (e.g., four bumps spaced at angular intervals of 90°) disposed on the inner surface of the bottom 511 along the circumferential directions thereof. As shown in FIG. 12, in the tip mounted state, the spacer 560 abuts against the distal end of the tip mounting part 5 to prevent the distal end of the tip mounting part 5 from contacting the test paper 530.

The spacer 560 is effective to protect the test paper 530 and also to prevent the blood spread on the test paper 530 from contacting and contaminating the tip mounting part 5.

The spacer 560 also has a function to abut against the distal end of the tip mounting part 5 in the tip mounted state to keep the test paper 530 and a light-emitting element 41 and a light-receiving element 42 of the photometric unit 4 spaced from each other by a constant distance. Consequently, measurement errors due to optical characteristic variations which would be caused if the distance varied are reduced, resulting in an increase in measurement accuracy.

The tip body 510 and the narrow tube 520 are made of a rigid material having a predetermined level of rigidity. The rigid material should preferably be any of highly hydrophilic materials such as acrylic resin or any of various hydrophilicized resin materials, for example.

The test paper 530 comprises a carrier capable of absorbing the blood (specimen) and a reagent (chromogenic reagent) carried on (impregnated in) the carrier. The carrier should preferably comprise a porous membrane (sheet-like porous base material). The porous membrane should preferably have such a pore diameter that red cells in the blood are filtered out.

The carrier of the test paper 530 may also comprise a sheet-like porous base material such as a nonwoven fabric, a woven fabric, a stretched sheet, or the like, other than the porous membrane.

The carrier such as the porous membrane may be made of any of polyesters, polyamides, polyolefins, polysulfons, celluloses, or the like. In order for the carrier to be impregnated with an aqueous solution of a reagent and to quickly absorb and spread the blood when the blood is sampled, the carrier should preferably be made of a hydrophilic material or a hydrophilicized material.

For measuring blood glucose levels, the reagent to be impregnated in the carrier (porous membrane) may be glucose oxidase (GOD), peroxidase (POD), or a chromogenic reagent such as 4-aminoantipyrine and N-ethyl-N-(2-hydroxy-3-sulfopropyl)-m-toluidine. Depending on a component to be measured, the reagent may be appropriately selected from other materials.

The test paper 530 has a central protrusion 531 and an annular protrusion 532 disposed outwardly of the protrusion 531 and projecting in the same direction as the protrusion 531. The annular protrusion 532 is in the form of a circular ring centering the protrusion 531, and has a distal end portion inserted in the specimen pool 550.

The annular protrusion 532 has a function to limit the spreading of the blood on the test paper 530. As a result, excessive blood is prevented from flowing out radially outwardly of the annular protrusion 532, and then, the tip 500 is prevented from being contaminated by blood contact.

FIG. 13 is a side elevational view showing the manner in which blood is sampled using the tip 500. As shown in FIG. 13, blood is sampled by puncturing a fingertip (or an earlobe) or the like with a needle, a scalpel, or the like to let a small amount (e.g., 1 to 6 μL) of blood B flow out from the punctured area onto the skin.

The tip 500 is installed on the tip mounting part 5 of the component measuring apparatus 1, and the end face of the specimen inlet end portion 521 of the narrow tube 520 is brought into abutment against the skin. The blood B on the fingertip flows through the groove 522 into the specimen inlet port 523, from which the blood B is absorbed according to the capillary action and flows through the specimen introducing passage 520a toward the proximal end thereof until it reaches the specimen outlet port 527. Since the blood B on the fingertip is effectively drawn in from the side openings of the groove 522 (the portions thereof which are open at the outer circumferential surface of the narrow tube 520), the blood B is not excessively spread over the skin and any blood loss is small.

The blood which has reached the specimen outlet port 527 is brought into contact with and absorbed by the protrusion 531 of the test paper 530. Some of the blood flows through the groove 526 into the gap 540. The blood flowing into the gap 540 is absorbed by the adjacent test paper 530 and spread thereon radially outwardly. As the blood B is absorbed by and spread on the test paper 530, and particularly absorbed in the vicinity of the protrusion 531, a new absorbing force is developed in the specimen introducing passage 520a, for thereby continuously supplying the blood B to the test paper 530.

When the spreading of the blood B on the test paper 530 is completed, a target component (e.g., glucose) in the blood B and the reagent carried in the test paper 530 react with each other, thereby producing a color depending on the amount of the target component. The color produced by the test paper 530 is colorimetrically measured to measure the intensity of the color for thereby determining the amount of the target component (blood glucose level) in the blood B.

Component measuring apparatus according to the present invention will be described in detail below based on preferred embodiments illustrated in the accompanying drawings.

<1st Embodiment>

A component measuring apparatus according to a first embodiment of the present invention will first be described below.

Figure 1:
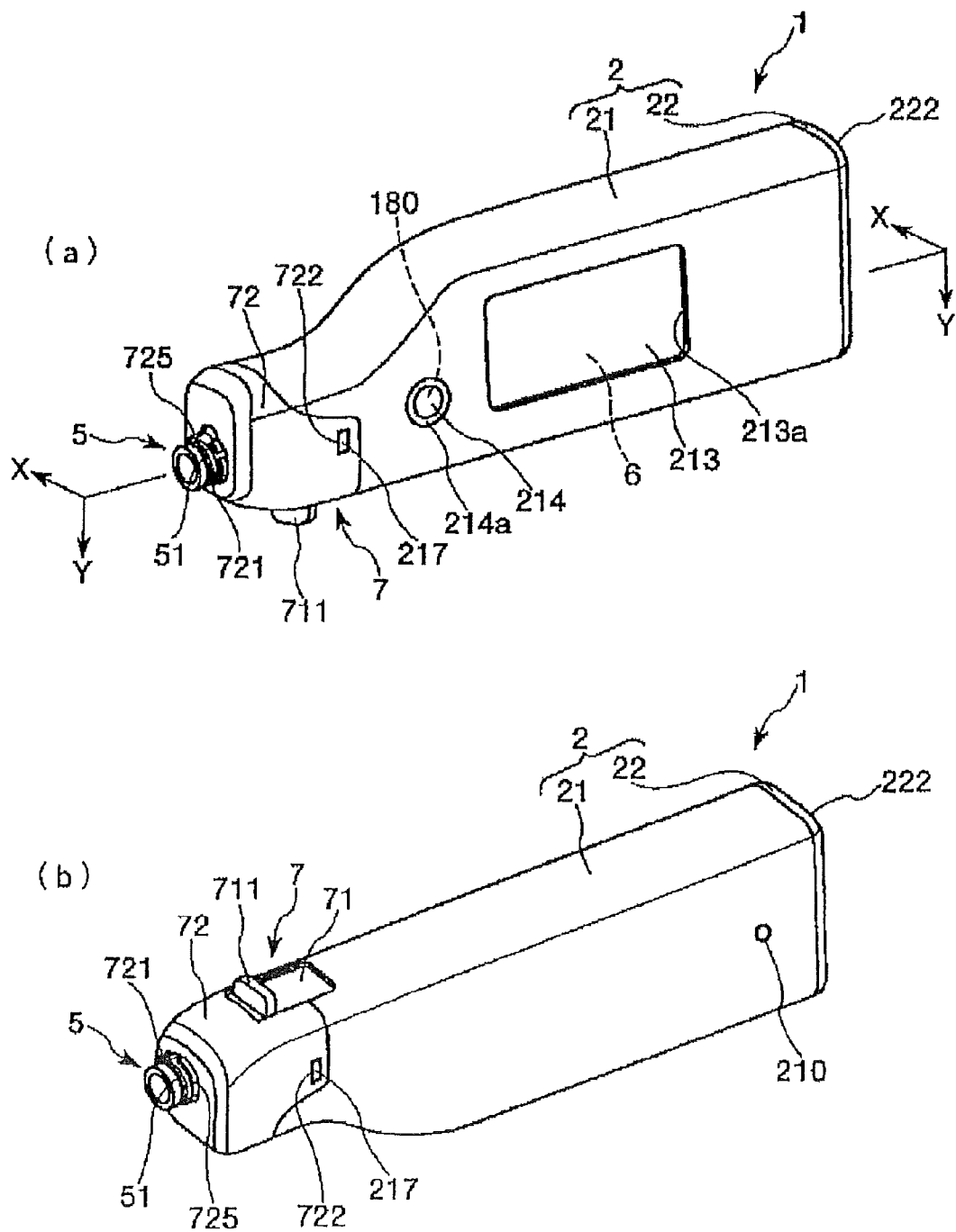
FIG. 1 is a set of perspective views ((a) is a front view and (b) a rear view) of a component measuring apparatus according to a first embodiment of the present invention.
Figure 2:
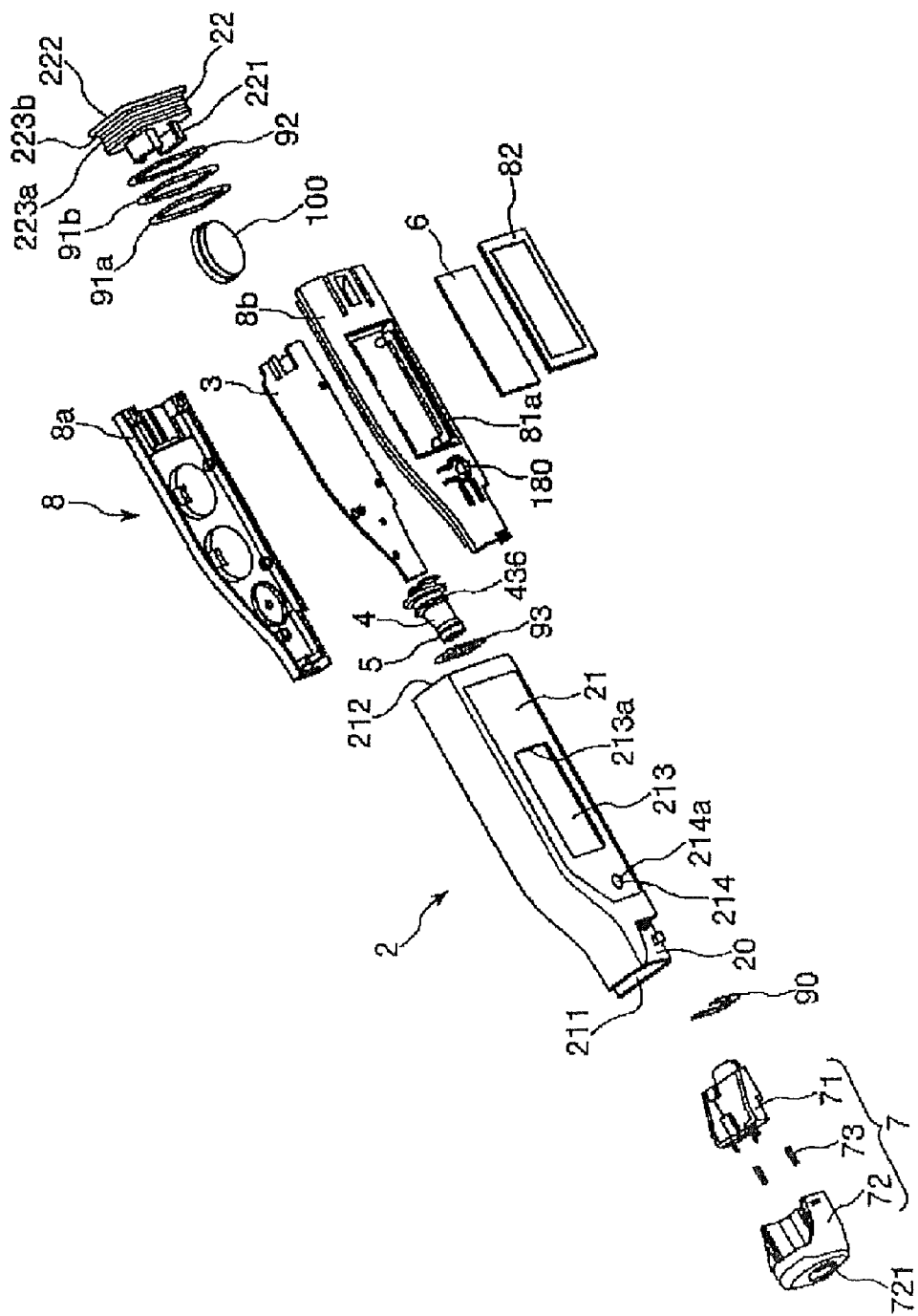
FIG. 2 is an exploded perspective view of the component measuring apparatus shown in FIG. 1.
Figure 3:
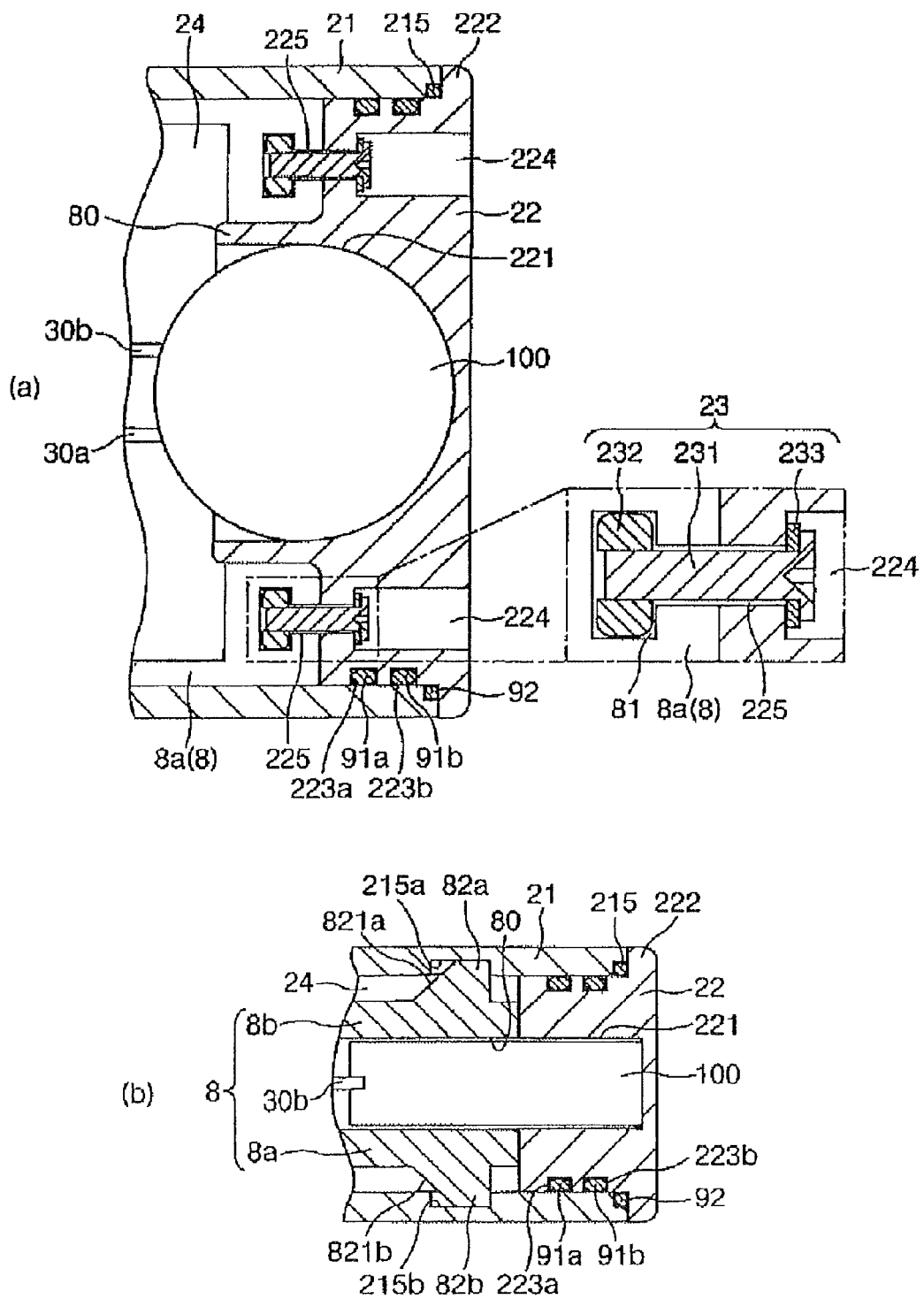
FIG. 3 is a set of vertical cross-sectional views of a proximal end portion of the component measuring apparatus shown in FIG. 1 ((a) is a cross-sectional view taken along line X-X of FIG. 1 and (b) a cross-sectional view taken along line Y-Y of FIG. 1)
Figure 4:
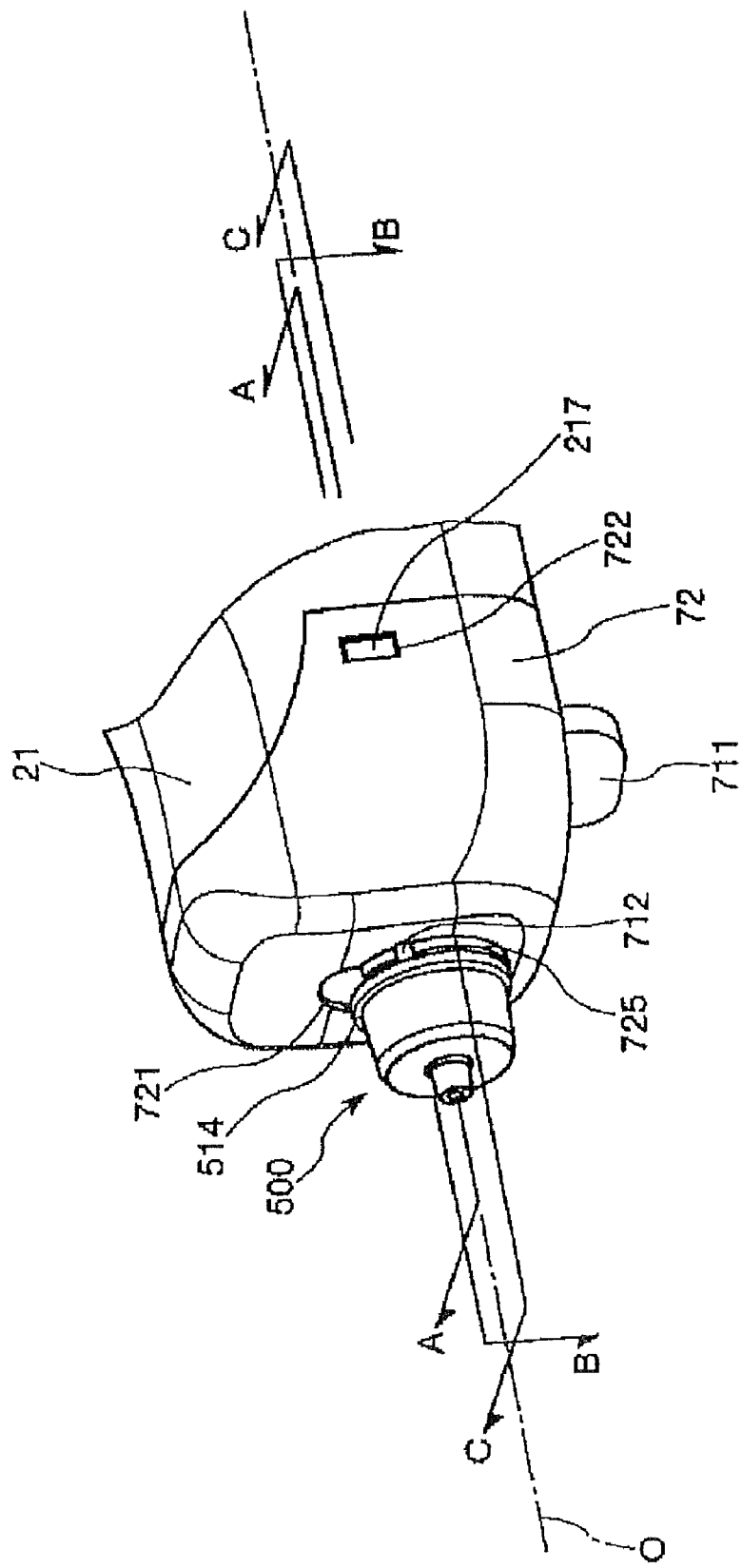
FIG. 4 is an enlarged perspective view of a distal end portion of the component measuring apparatus shown in FIG. 1.
Figure 5:
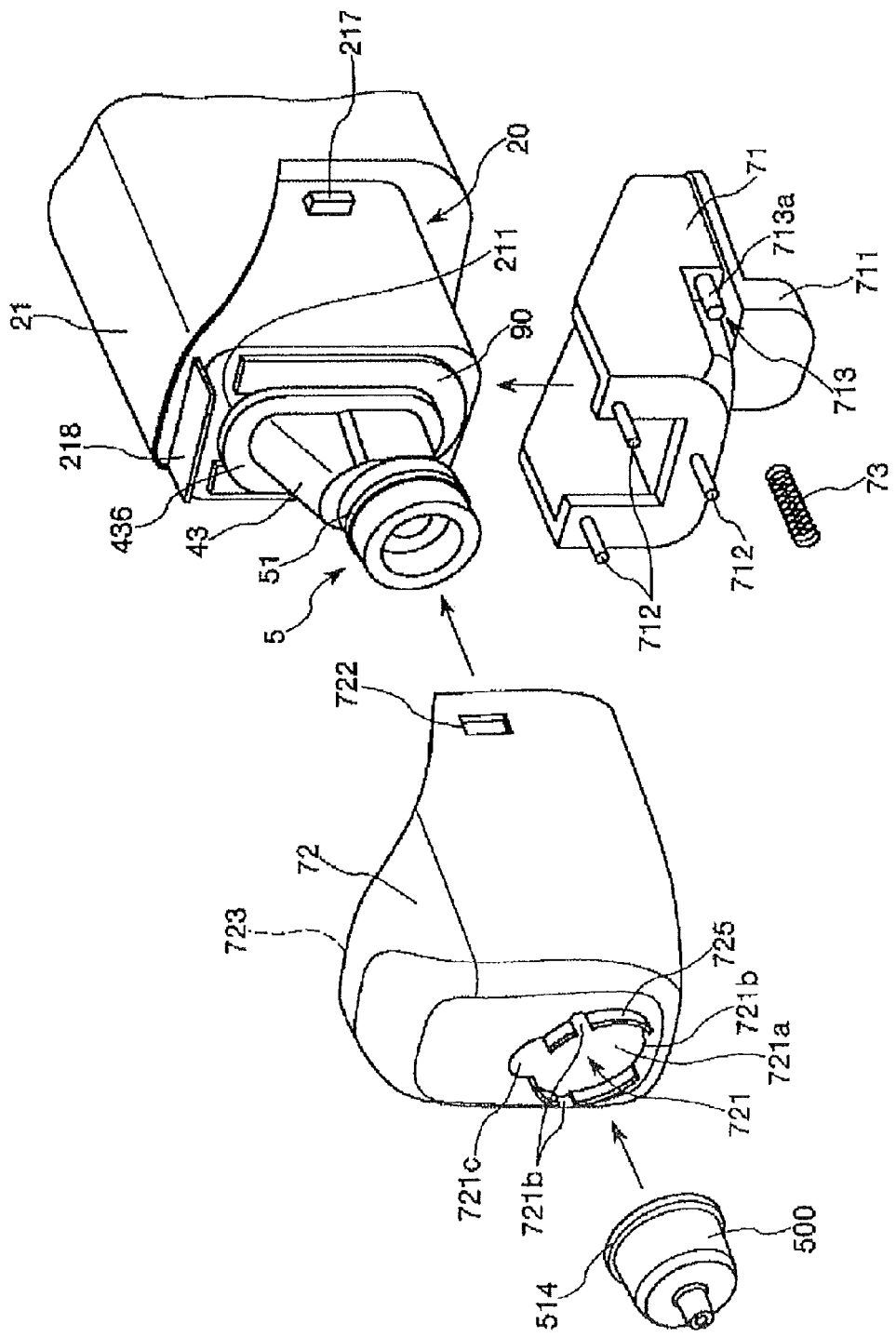
FIG. 5 is an exploded perspective view of the distal end portion shown in FIG. 4.
Figure 6:
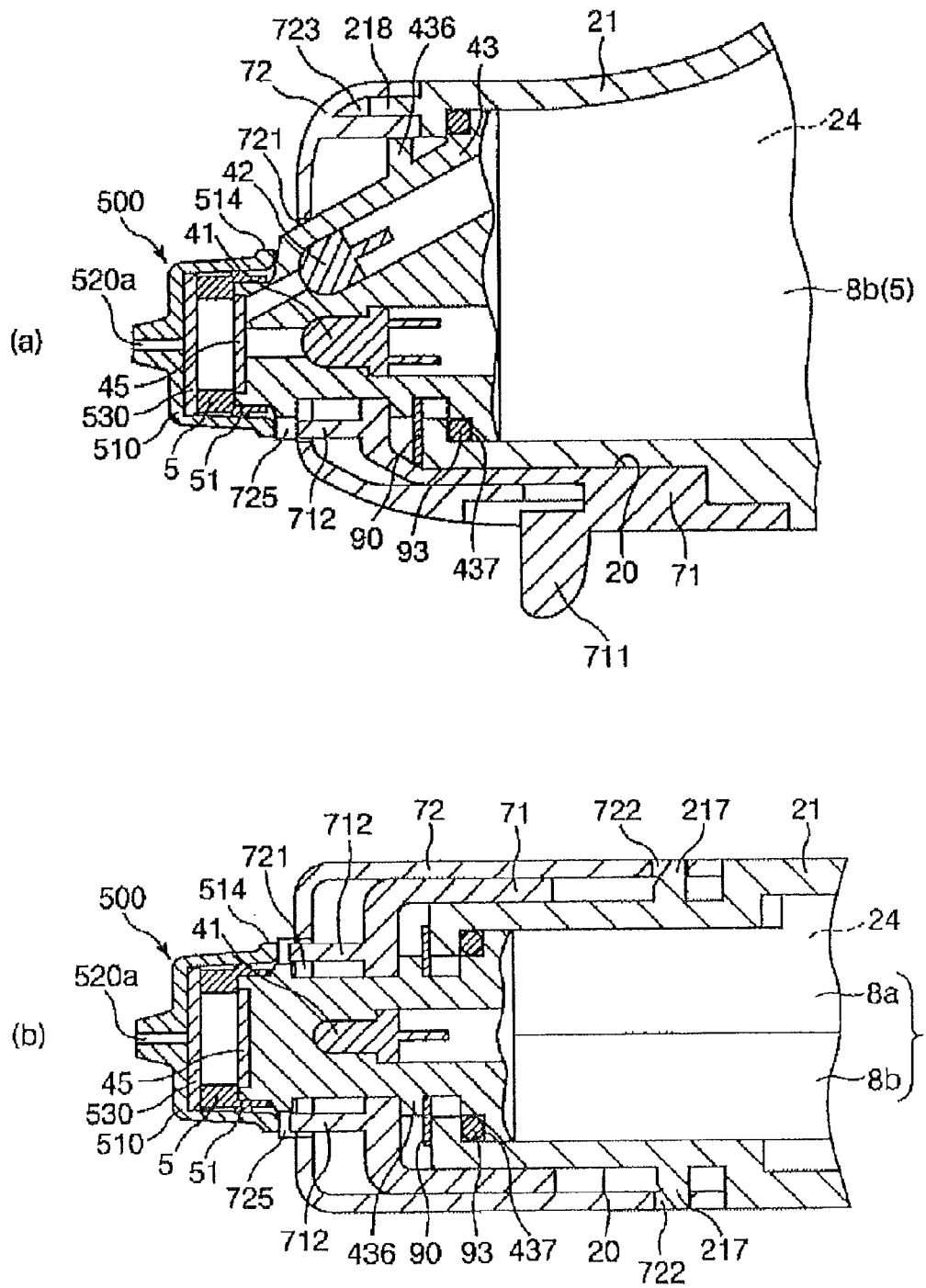
FIG. 6 is a set of vertical cross-sectional views of the distal end portion shown in FIG. 4 ((a) is a cross-sectional view taken along line A-A of FIG. 4 and (b) is a cross-sectional view taken along line B-B of FIG. 4)
Figure 7:
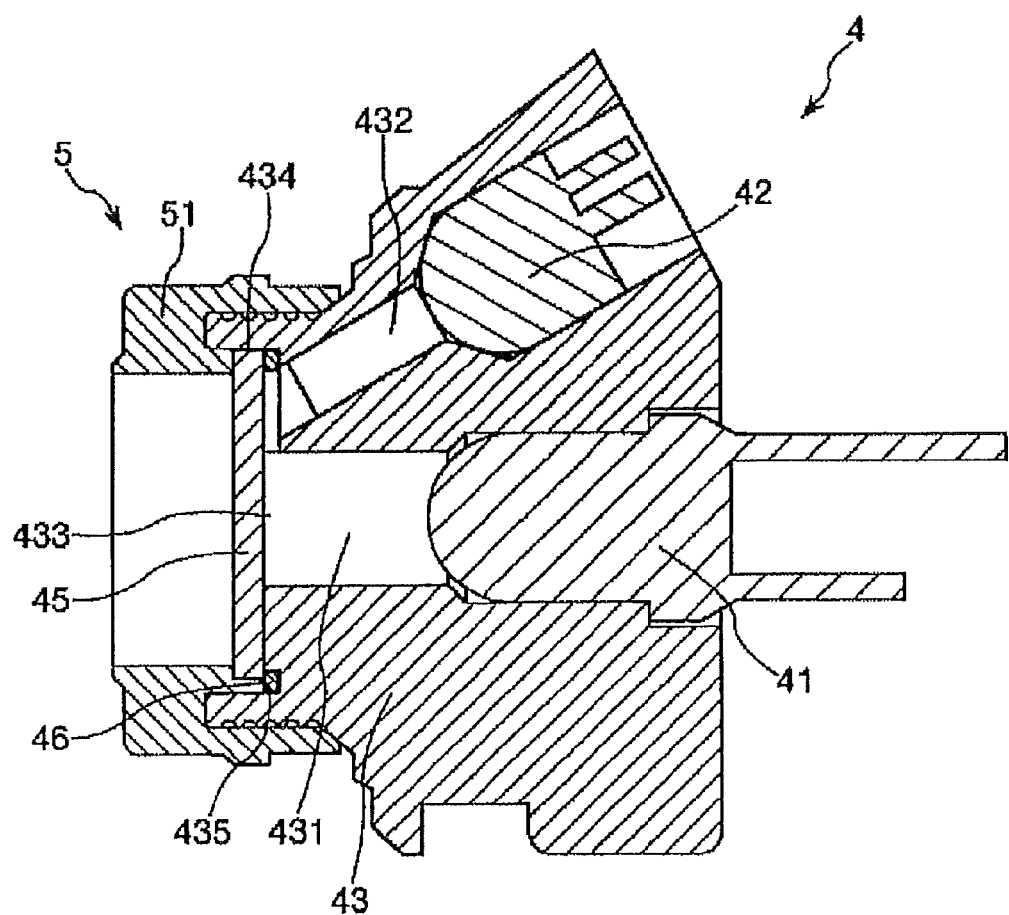
FIG. 7 is a vertical cross-sectional view showing structural details of a photometric unit of the component measuring apparatus shown in FIG. 1.
Figure 8:
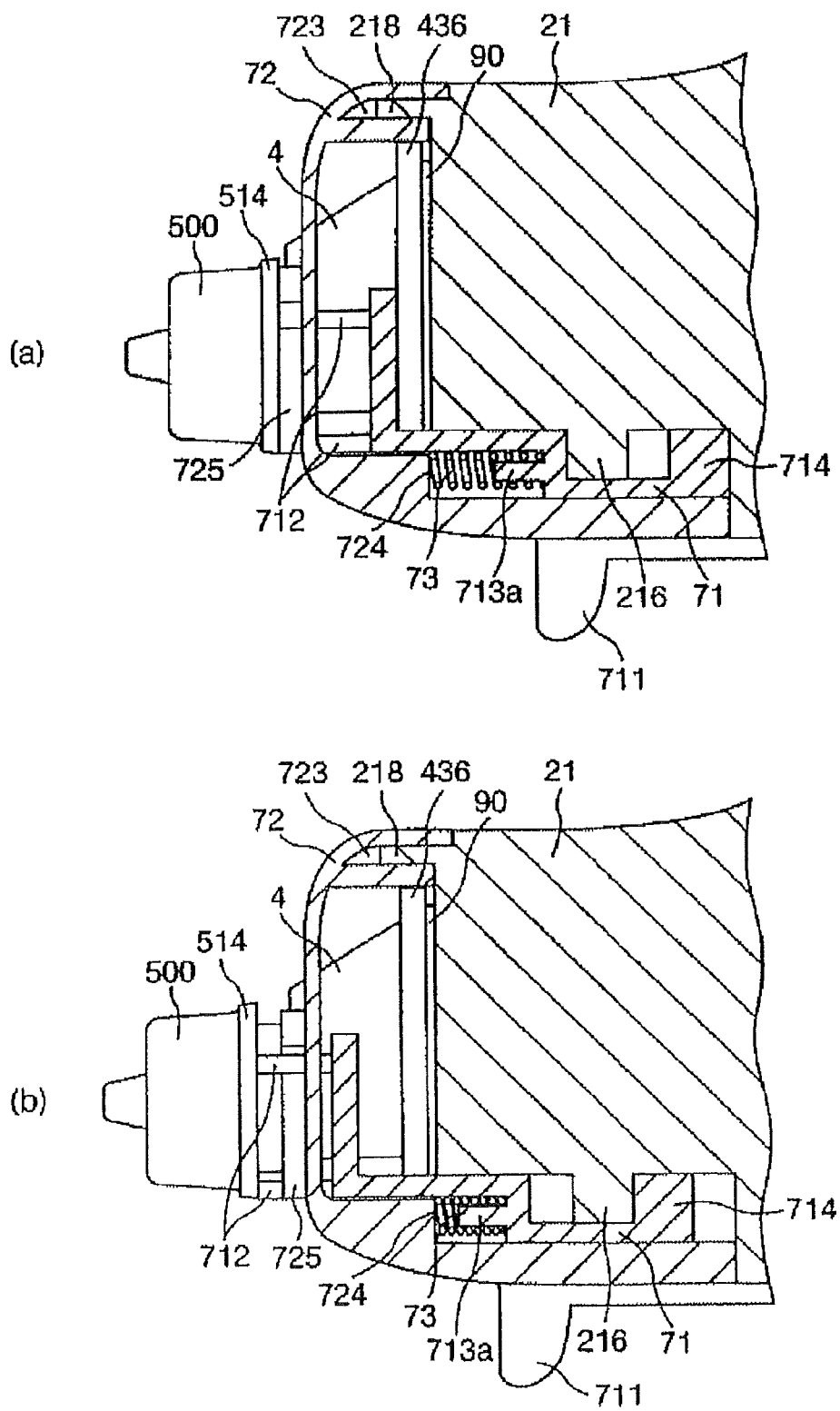
FIG. 8 is a set of cross-sectional views taken along line C-C of FIG. 4 ((a) shows an initial state and (b) shows an operational state)
Figure 9:
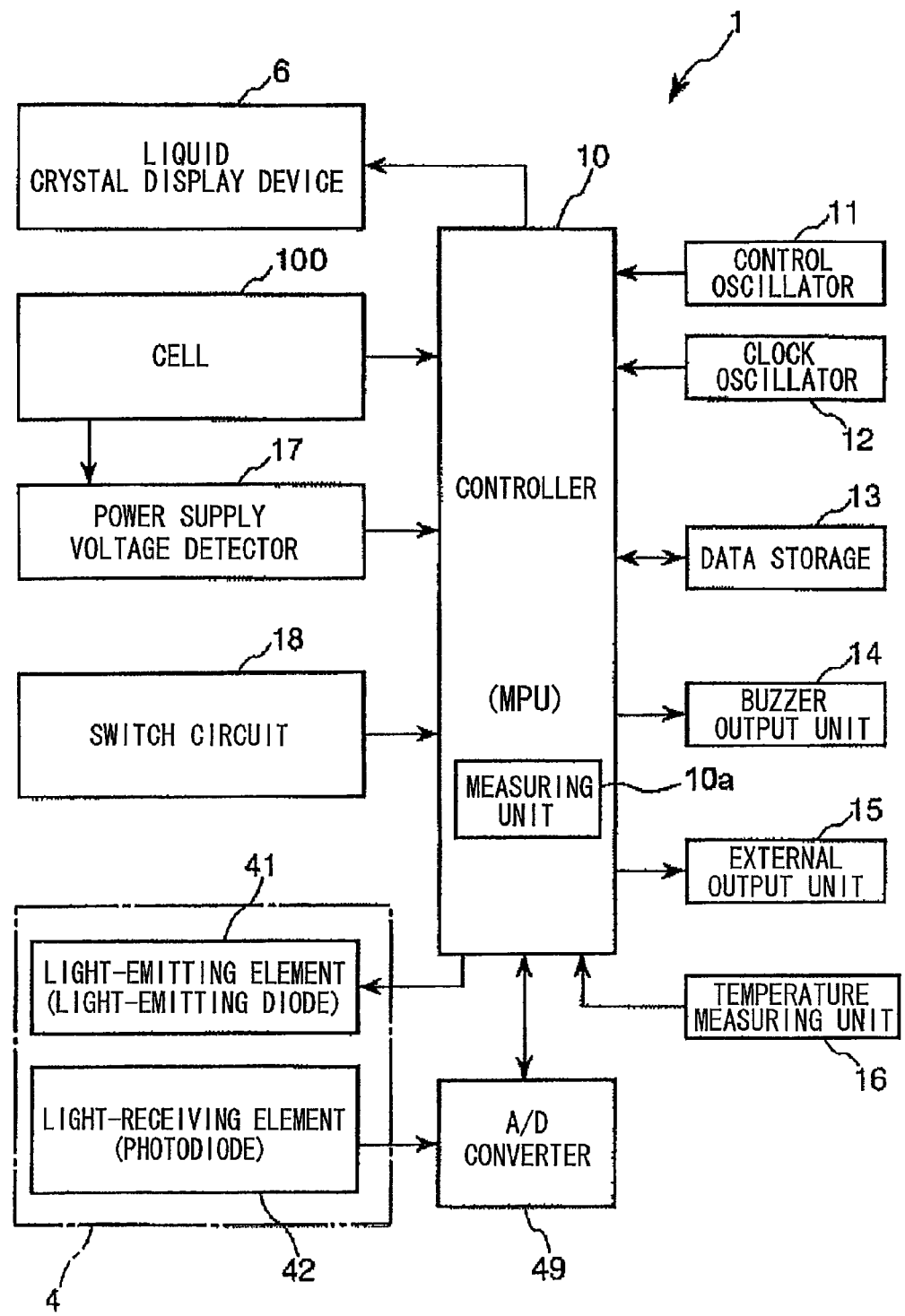
FIG. 9 is a block diagram of the component measuring apparatus shown in FIG. 1.

FIG. 1 is a set of perspective views ((a) is a front view and (b) a rear view) of the component measuring apparatus according to the first embodiment of the present invention. FIG. 2 is an exploded perspective view of the component measuring apparatus shown in FIG. 1. FIG. 3 is a set of vertical cross-sectional views of a proximal end portion of the component measuring apparatus shown in FIG. 1 ((a) is a cross-sectional view taken along line X-X of FIG. 1 and (b) a cross-sectional view taken along line Y-Y of FIG. 1). FIG. 4 is an enlarged perspective view of a distal end portion of the component measuring apparatus shown in FIG. 1. FIG. 5 is an exploded perspective view of the distal end portion shown in FIG. 4. FIG. 6 is a set of vertical cross-sectional views of the distal end portion shown in FIG. 4 ((a) is a cross-sectional view taken along line A-A of FIG. 4 and (b) is a cross-sectional view taken along line B-B of FIG. 4). FIG. 7 is a vertical cross-sectional view showing structural details of a photometric unit of the component measuring apparatus shown in FIG. 1. FIG. 8 is a set of cross-sectional views taken along line C-C of FIG. 4 ((a) shows an initial state and (b) shows an operational state). FIG. 9 is a block diagram of the component measuring apparatus shown in FIG. 1. In FIGS. 1 to 8 (and also FIG. 10), a right side will be described as "proximal end" and a left side as "distal end".

The component measuring apparatus (blood component measuring apparatus) 1 according to the present invention is used with the tip 500 described above being mounted thereon. The component measuring apparatus 1 shown in each of the figures comprises a case 2, a printed-circuit board 3 disposed in the case 2, a photometric unit (detector) 4 disposed in a distal end portion of the case 2, a tip mounting part 5 fixed to a distal end of the photometric unit 4, a liquid crystal display device (display) 6 disposed in the case 2, and an ejector mechanism 7 disposed outside of the case 2.

As shown in FIG. 2, the case 2 comprises a case body 21 and a lid 22.

The case body 21 comprises a tubular member and has a distal-end opening 211 and a proximal-end opening 212. The case body 21 has a substantially rectangular cross section (transverse cross section) in a direction perpendicular to its longitudinal direction.

The case body 21 has an opening (window) 213a formed in a side surface (front surface) thereof at a position corresponding to the liquid crystal display device 6 to be described later. In the opening 213a, there is fixedly mounted a light-permeable member (window) 213 having light permeability such that hermetic sealing is maintained (secured) between the light-permeable member 213 and the case body 21.

The component measuring apparatus 1 allows display contents (measurement results) displayed on the liquid crystal display device 6 to be visually recognized through the light-permeable member 213.

The light-permeable member 213 may be fixed to the case body 21 by fusion bonding (thermal fusion, high-frequency fusion, ultrasonic fusion), adhesive bonding, multicolor molding, or the like, for example.

The case body 21 also has a through hole 214a formed in the side surface (front surface) thereof more closely to the distal end than the opening 213a, for a portion (operating button (pressing button) 180) of a power supply switch, to be described later, to be inserted therein. The through hole 214a is hermetically sealed by an elastic member 214 in the form of a flat plate.

The elastic member 214 may be fixed to the case body 21 in the same manner as the light-permeable member 213 is fixed to the case body 21. It is preferable to employ multicolor molding among other things. The multicolor molding allows the elastic member 214 and the case body 21 to be formed integrally with each other.

The elastic member 214 is repeatedly deformed when the operating button 180 is pressed. The elastic member 214 which is molded integrally with the case body 21 by multicolor molding is prevented from being peeled off the case body 21 to reliably keep hermetic sealing between the elastic member 214 and the case body 21 for a long period of time.

The case body 21 has an inspection through hole 210 formed in a side surface (rear surface) thereof for connection to an inspecting device (e.g., a pressure gage, a pressurization/suction nozzle, a leak detection gas introducing nozzle, or the like) for inspecting the component measuring apparatus 1 for hermetic sealing (see FIG. 1(b)). After the component measuring apparatus 1 is assembled, the distal end portion (measuring part) of the inspecting device is connected to the inspection through hole 210 for inspecting the component measuring apparatus 1 for its level of hermetic sealing (liquid tightness, air tightness).

When the component measuring apparatus 1 is in use, the inspection through hole 210 is hermetically sealed by a hermetic sealing means for thereby providing hermetic sealing in the case 2 unless necessary (inspection for hermetic sealing).

The hermetic sealing means may be an elastic plug (sealing member) press-fitted in the inspection through hole 210, a washer screw (sealing member), to be described later, screwed in the inspection through hole 210, or the like. The plug or the washer may be made of a material which is the same as the material of an O-ring to be described later.

As shown in FIGS. 1 to 3, the lid 22 is detachably mounted on the case body 21 so as to close the proximal-end opening 212. The lid 22 comprises a member in the form of a substantially rectangular parallelepiped, and is inserted (fitted) in the case body 21 through the proximal-end opening 212.

The lid 22 has a recess 221 which is open toward its distal end (see FIG. 3, for example). The recess 221 serves as a cell mounting part for mounting a cell (button cell) 100 thereon. With the cell mounting part on the lid 22, i.e., with the cell mounting part integrally formed (or joined) with the lid 22, the number of parts constituting the component measuring apparatus 1 is reduced, and the cell 100 can be replaced with ease.

A plate-like flange 222 projecting outwardly is integrally formed with the lid 22 at the proximal end portion of the recess 221. With the lid 22 attached to the case body 21, the flange 222 abuts against the proximal end of the case body 21 to prevent the lid 22 from moving with respect to the case body 21, i.e., to position the lid 22 with respect to the case body 21.

The state in which the printed-circuit board 3, etc. to be described later is housed in the case body 21, the lid 22 is attached to the case body 21, and the ejector mechanism 7 is attached to the case body 21, i.e., the state shown in FIGS. 1, 3, 4, and 6, is referred to as an "assembled state".

In the assembled state, as shown in FIG. 3, the lid 22 is essentially housed in the case body 21 and fixed by a fixing means 23 to an inner case 8 that is fixed to the case body 21.

Specifically, the inner case 8 has a recess 81 formed in the proximal end portion thereof, and the lid 22 has a recess 224 that is open toward the proximal end thereof. A communication hole 225 communicating between the recess 81 and the recess 224 is formed continuously in the inner case 8 and the lid 22 (see FIG. 3(a)).

The recess 81 houses a nut 232 therein, and a screw 231 is inserted through the recess 224 and the communication hole 225 and threaded into the nut 232, thereby fixing the lid 22 to the case body 21 through the intermediary of the inner case 8.

A ring-shaped washer (annular elastic plate) 233 is disposed between the head of the screw 231 and the bottom (distal end surface) of the recess 224 to provide hermetic sealing in the corresponding region in the case 2 in the assembled state.

The lid 22 has a plurality of (two in the present embodiment) ring-shaped grooves (fitting regions) 223a, 223b formed in a circumferential surface thereof and spaced a predetermined distance from each other in the axial directions (left and right directions in FIGS. 2 and 3). The case body 21 has a step 215 on the proximal end thereof which extends along an inner edge thereof.

In the assembled state, O-rings 91a, 91b are disposed respectively in the grooves 223a, 223b and an O-ring 92 is disposed on the step 215. In other words, the O-rings 91a, 91b, 92 are disposed between the case body 21 and the lid 22 near the proximal-end opening 212, thereby providing hermetic sealing between the case body 21 and the lid 22. The O-rings (annular elastic members (second annular members)) 91a, 91b, 92 serve as a second hermetic sealing means.

The printed-circuit board 3 is disposed (housed) in the case 2. The printed-circuit board 3 supports thereon a controller 10 comprising a microcomputer for controlling various modes of operation of the component measuring apparatus 1 including operation of the photometric unit 4 to be described later.

The controller 10 includes a measuring unit (processor) 10a for measuring (calculating) a target blood component (e.g., glucose) based on the signal from the photometric unit 4. The measuring unit 10a performs hematocrit level correcting calculations, temperature correcting calculations, etc. if necessary.

The photometric unit (detector) 4 is electrically connected to the controller 10. Specifically, the photometric unit 4 has a light-emitting element (light-emitting diode) 41 and a light-receiving element (photodiode) 42 which are housed and held in a holder (tubular member) 43 (see FIG. 7). The light-emitting element 41 is electrically connected to the controller 10, and the light-receiving element 42 is electrically connected to the controller 10 through an amplifier, not shown, and an A/D converter 49 (see FIG. 9).

The photometric unit 4 has a function to photometrically measure (detect) a color developed depending on the glucose level of the blood. According to the present embodiment, as shown in FIGS. 6 and 8, the photometric unit 4 is disposed near the distal-end opening 211 of the case body 21 such that a distal end portion (a portion) of the holder 43 (the photometric unit 4) projects out of the distal-end opening 211 of the case body 21.

The holder 43, the case body 21, the lid 22, an ejector member 71, a distal-end cover member 72, and a fitting member 90, to be described later, are made of any of various resin materials including acrylic resin, polystyrene, polyethylene, polypropylene, hard polyvinyl chloride, polycarbonate, polymethyl methacrylate, ABS resin, polyester, polyphenylene sulfide (PPS), polyamide, polyimide, polyacetal, etc., and a polymer alloy, a polymer blend, and the like which include one or more of the above materials, or any of various metal materials including aluminum, aluminum alloy, titanium, titanium alloy, stainless steel, etc.

As shown in FIGS. 6 and 7, the holder 43 has a first passage 431 formed therein for passing and guiding a light beam emitted by the light-emitting element 41 therethrough to the test paper 530, and a second passage 432 formed therein for passing and guiding a light beam reflected by the test paper 530 to the light-receiving element 42.

The first passage 431 and the second passage 432 are joined to (combined with) each other at a distal end portion of the holder 43, and are open at the distal end of the holder 43. An opening 433 where the first passage 431 and the second passage 432 are open is formed in the distal end of the holder 43.

The opening 433 should preferably be circular in shape, but may be of a shape that is selected, as necessary, from an elliptical shape, a quadrangular shape including a square shape, a rectangular shape, a rhomboidal shape, and the like, a triangular shape, a hexagonal shape, an octagonal shape, and the like, for example.

A recess 434 with the opening 433 positioned substantially centrally therein is formed in the distal end portion of the holder 43 (which faces the test paper 530 in the tip mounted state).

An annular recess 435 is formed in an outer circumferential portion of the recess 434. The annular recess 435 is deeper than the recess 434 and held in communication with the recess 434.

An O-ring 46 is placed in the annular recess 435, and a light-permeable member 45 is housed and fixed in the recess 434. The first passage 431 and the second passage 432 (hereinafter simply referred to as "passage") in the holder 43 are hermetically sealed by the light-permeable member 45 with the O-ring 46 interposed therebetween.

The light-permeable member 45 may be fixed (fastened) to the holder 43 by fitting engagement, fusion bonding, thread engagement, adhesive bonding, or the like, for example.

The light-permeable member 45 has a thickness (average) which varies slightly depending on the material thereof and should not be limited to any particular value. However, the thickness of the light-permeable member 45 should preferably be in the range from about 0.1 to 10 mm and more preferably from about 0.3 to 3 mm. If the light-permeable member 45 is too thin, its mechanical strength would be lowered. If the light-permeable member 45 is too thick, then the photometric unit 4 would be undesirably large in size.

The light-permeable member 45 should preferably be of a shape corresponding to the opening 433 and may have such a dimension that the opening 433 is covered.

The light-permeable member 45 may be made of any of various glass materials and various resin materials, etc., for example. The light-permeable member 45 is not limited to a flat plate shape, but may be of a lens shape, for example.

The light-permeable member 45 may have, on its surface, one or more coating layers for any desired purposes. For example, coating layers may be provided for the purpose of increasing measurement accuracy, for the purpose of preventing the light-permeable member 45 from being scratched, etc.

Coating layers for increasing measurement accuracy should preferably include, for example, an antireflection coating (AR coating) for preventing the light beam emitted from the light-emitting element 41 from being reflected by the surface (proximal-end surface) of the light-permeable member 45, and an antireflection coating for preventing the light beam reflected by the test paper 530 from being reflected by the surface (distal-end surface) of the light-permeable member 45. Since ambient light (particularly infrared radiation) has a great influence on the measurement accuracy, it is preferable to provide a low-pass filter for selectively passing light having a wavelength of 720 nm or shorter, a bandpass filter for selectively passing light having wavelengths ranging from about 500 to 720 nm (corresponding to the wavelengths of light emitted by the light-emitting element 41), or the like, for example.

Coating layers for preventing the light-permeable member 45 from being scratched should preferably include reinforced coating layers (hard coating layers) mainly made of an Si-based material, an Al-based material, a polyfunctional acrylic material, a urethane-resin-based material, a melamine-resin-based material, etc., for example.

The O-ring 46 is made of an elastic material and has a diameter in its vertical cross section greater than the depth of the annular recess 435. With the light-permeable member 45 placed in the recess 434, the O-ring 46 is reliably held in close contact with both the holder 43 and the light-permeable member 45, thereby achieving an increased level of hermetic sealing (liquid tightness, air tightness) in the passages of the holder 43.

Constituent materials (elastic materials) of the O-ring 46, the O-rings 91a, 91b, 92, and an O-ring 93 to be described later are not limited to particular materials, but may include various rubber materials (particularly, vulcanized materials) such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, fluororubber, etc., and various thermoplastic elastomers such as styrene elastomer, polyolefin elastomer, polyvinyl chloride elastomer, polyurethane elastomer, polyester elastomer, polyamide elastomer, polybutadiene elastomer, transpolyisoprene elastomer, fluororubber elastomer, chlorinated polyethylene elastomer, etc. One of these materials or a mixture of two or more of these materials may be used.

The O-ring 46 is not limited to being placed in the illustrated position, but may be disposed on the outer circumferential surface of the light-permeable member 45.

The light-emitting element 41 is energized in response to a signal from the controller 10 to emit light beam pulses at predetermined time intervals. The light beam pulses have a cyclic period in the range from about 0.5 to 3.0 msec., and each of the light beam pulses has an emission time in the range from about 0.05 to 0.3 msec.

The light beam pulses have a wavelength which should preferably be in the range from about 500 to 720 nm and more preferably from about 580 to 650 nm.

The tip mounting part 5 on which the tip (component measuring tip) 500 incorporating the test paper 530 described above is detachably mounted, is fixed to the distal end portion of the holder 43 (the photometric unit 4). The tip mounting part 5 does not need to be integrally formed with the case body 21, and hence the component measuring apparatus 1 is simplified in structure and reduced in manufacturing cost.

The tip mounting part 5 comprises a hollow cylindrical member and projects outwardly through a distal-end opening 721 of the distal-end cover member 72.

The portion of the tip mounting part 5 which projects from the distal-end cover member 72 has the fitting portion 51 in the form of a ring that projects outwardly. In the tip mounted state, the fitting portion 51 is fitted in the proximal end portion of the tip body 510, thereby fixing the tip 500 to the component measuring apparatus 1.

The openings of the first passage 431 and the second passage 432 are positioned inside the tip mounting part 5. In the tip mounted state, therefore, the distal end face of the holder 43 confronts (faces) the test paper 530 of the tip 500. When the light-emitting element 41 is turned on in this state, the light beam emitted from the light-emitting element 41 is applied to the test paper 530, which reflects the light beam. The reflected light beam is received by the light-receiving element 42 and photoelectrically converted thereby. The light-receiving element 42 outputs an analog signal depending on the intensity of the received light beam. The analog signal is amplified at a desired level and then converted by the A/D converter 49 into a digital signal, which is input to the controller 10.

As shown in FIG. 6(a), the outer circumferential surface of the holder 43 has a ring-shaped (annular) step 437 at a certain position in the longitudinal direction thereof. In the assembled state, the step 437 is positioned in the case body 21, and an O-ring (annular elastic member (first elastic member)) 93 is disposed on the step 437. In other words, the O-ring 93 is disposed between the case body 21 and the photometric unit 4 near the distal-end opening 211.

The O-ring 93 is held in close contact with the case body 21 and the photometric unit 4, thereby providing hermetic sealing in the corresponding region in the case body 21. The O-ring 93 serves as a first hermetic sealing means.

In the assembled state, the photometric unit 4 (the holder 43) has a portion projecting outwardly (exposed) from the case 2 through the distal-end opening 211. In the corresponding region, the holder 43 has, on its outer circumferential surface, a ring-shaped flange 436 at a certain position in the longitudinal direction of the portion which projects from the case body 21 (see FIG. 5, for example). In other words, the portion of the photometric unit 4 which projects from the case 2 has the flange 436 which projects outwardly substantially perpendicularly to the axial directions of the case body 21.

In the assembled state, a fitting member (spacer) 90 is fitted between the flange 436 and the distal end of the case body 21. The fitting member 90 comprises a flat plate member which is substantially U-shaped, and the fitting member 90 is inserted (fitted) between the flange 436 and the distal end of the case body 21 from below in FIG. 5.

The photometric unit 4 is thus moved toward the distal end with respect to the case body 21. As a result, the O-ring 93 is compressed, thereby achieving more close contact thereof with the case body 21 and the photometric unit 4. Accordingly, better hermetic sealing is provided in the case 2 by the O-ring 93 with a simple arrangement. Therefore, the fitting member 90 can function as a means for increasing (intensifying) pressing and closing forces (hermetic sealing forces) of the O-ring 93.

Even if a dimensional error occurs between the case body 21 and the photometric unit 4 (the holder 43) at the time the component measuring apparatus is manufactured, the fitting member 90 is effective to enable the O-ring 93 to provide reliable hermetic sealing in the case 2.

The fitting member 90 may alternatively be V-shaped, C-shaped, or the like, for example.

As shown in FIG. 2, the printed-circuit board 3 is housed in the inner case 8 with the photometric unit 4 fixed to the distal end portion thereof, the assembly being disposed in the case 2.

The inner case 8 comprises a pair of halves, i.e., a first member 8a and a second member 8b, with the printed-circuit board 3 sandwiched (fixed) therebetween. With the printed-circuit board 3 sandwiched (disposed) between the first member 8a and the second member 8b, i.e., with the inner case 8 assembled, the inner case 8 has a proximal-end opening 80 formed in the proximal end thereof (see FIG. 3). The recess 81 referred to above is formed in an outer circumferential portion around the proximal-end opening 80.

In the assembled state, the distal end of the lid 22 with the cell 100 mounted therein is inserted into the inner case 8 through the proximal end opening 80. The proximal end portion of the printed-circuit board 3 has a pair of terminals (electric connectors) 30a, 30b, which is connected to the cell 100 in the assembled state (see FIG. 3). The controller 10 is thus supplied with electric power.

As shown in FIG. 3(b), the first member 8a and the second member 8b have respective proximal end portions including respective projections 82a, 82b projecting outwardly. The case body 21 has recesses 215a, 215b formed in respective inner surfaces of the proximal end portion thereof. In the assembled state, the projections 82a, 82b are inserted and fitted in the recesses 215a, 215b, respectively, thereby fixing the inner case 8 to the case body 21.

The projections 82a, 82b have respective slanted surfaces 821a, 821b on their distal ends for thereby allowing the inner case 8 to be inserted into the case body 21, i.e., for thereby assembling the component measuring apparatus 1, easily.

As shown in FIG. 2, the second member 8b has an opening 81a formed therein. The liquid crystal display device 6 is disposed in the opening 81a and fixed to the second member 8b by a frame member 82.

A control oscillator 11, a clock oscillator 12, a data storage 13, a buzzer output unit 14, an external output unit 15, a temperature measuring unit 16, a power supply voltage detector 17, and a switch circuit 18 are disposed in their respective predetermined locations in the inner case 8 (the component measuring apparatus 1) (see FIG. 9).

The control oscillator 11, which serves as a timer, generates clock pulses at constant time intervals and supplies an operation reference signal for a microcomputer (microprocessing unit: MPU) of the controller 10.

The clock oscillator 12, which serves as a clock for providing absolute time (date and time), generates clock pulses at constant time intervals and supplies an operation reference signal for a time control circuit incorporated in the controller 10.

The data storage 13 includes a first memory (RAM), a second memory (ROM), and a third memory (non-volatile RAM). Photometric values (photometric data) input from the photometric unit 4 are stored into the first memory according to a predetermined format.

The second memory stores a previously-determined table representing the relationship (calibration curve) between absorbance values determined from the photometric values and amounts of target blood components.

The third memory stores inherent calibration values for individual apparatus. The inherent calibration values include prescribed values of the amount of the reflected light beam, corrective coefficients for absorbance calculations, etc.

The buzzer output unit 14 operates a buzzer to produce sound based on a signal from the controller 10.

The external output unit 15 serves to output data representative of the determined amount of a target blood component, etc. to an external device such as a personal computer, for example. The external output unit 15 incorporates a communication driver such as RS232C, for example. For infrared communications, the external output unit 15 incorporates an infrared-emitting element and a drive circuit therefor.

The temperature measuring unit 16 has a temperature sensor (thermistor) for measuring the ambient temperature. The temperature measuring unit 16 measures the temperature occasionally and stores its temperature information into the first memory of the data storage 13. The temperature information read from the first memory is input to the controller 10, which uses the temperature information in calculations for temperature-correcting the amount of the target blood component.

The power supply voltage detector 17 detects the voltage of the cell 100 and outputs the detected voltage value (detected value) to the controller 10 for checking a remaining battery level of the cell 100.

The switch circuit 18 detects input signals from various switches described below, and inputs the signals to the controller 10. The switches include a power supply switch, a stored data readout switch, a time setting/changing switch, a resetting switch, a buzzer activation/inactivation selector switch, a 50 Hz/60 Hz commercial power supply frequency selector switch, etc.

The power supply switch can turn on and off the component measuring apparatus 1 when the operating button 180 is pressed. Alternatively, the operating button 180 may be omitted, and the liquid crystal display device 6 may comprise a touch panel whose display screen may be touched to turn on and off the component measuring apparatus 1.

If the liquid crystal display device 6 comprises a touch panel, then the light-permeable member 213 is omitted, and an O-ring (ring-shaped elastic member) is disposed in the case body 21 and between the case body 21 and the liquid crystal display device 6 near the opening 213a to provide hermetic sealing in the case 2. Specifically, the frame member 82 may be made of an elastic material.

As shown in FIG. 6, a recess 20 is formed in an outer surface of the distal end portion of the case 2 (the case body 21). The ejector mechanism 7 for removing the tip 500 mounted on the tip mounting part 5 from the tip mounting part 5 is disposed in the recess 20.

As shown in FIGS. 2 and 3, the ejector mechanism 7 comprises an ejector member 71, a distal-end cover member 72, and a return spring 73.

The ejector member 71 is disposed in the recess 20 and movable in the axial directions of the case 2. The ejector member 71 comprises a member having a C-shaped vertical cross section.

The ejector member 71 has, on its front face, rod-like pins (abutment portions) 712 projecting toward the distal end. In the present embodiment, the ejector member 71 has three pins 712. When the tip 500 mounted on the tip mounting part 5 is to be removed, the distal ends of the pins 712 abut against the proximal end (the flange 514) of the tip 500 (see FIG. 8(b)).

In the assembled state, the pins 712 are disposed at substantially equal angular intervals along the circumferential directions about the axis (central axis O) of the case 2. When the ejector member 71 is operated to remove the tip 500, the tip 500 is pressed uniformly in the circumferential directions. Therefore, the ejector member 71 can be operated (to remove the tip 500) reliably.

The ejector member 71 also has, on its lower surface, a finger hook 711 projecting downwardly. The finger hook 711 is engaged by a finger to move the ejector member 71, i.e., to remove the tip 500 from the tip mounting part 5.

A pair of recesses 713, 713 is formed in a lower portion of the distal end of the ejector member 71. A rod-shaped protrusion 713a projects from the proximal end surface of each of the recesses 713 toward the distal end. The protrusion 713a is inserted in the proximal end portion of the return spring 73.

As shown in FIG. 8, an engaging portion 714 is formed such that the engaging portion 714 projects upwardly from the proximal end portion of the ejector member 71. An engaging portion 216 is formed such that the engaging portion 216 projects downwardly from a lower portion of the case body 21. When the ejector member 71 is moved toward the distal end, the engaging portion 714 engages with the engaging portion 216 to prevent the ejector member 71 from being moved toward the distal end.

The ejector member 71 is housed in the distal-end cover member 72 which is fixed to the distal end portion of the case 2 (the case body 21). The distal-end cover member 72 functions to guide the ejector member 71 for movement. Therefore, the ejector member 71 can be moved accurately.

The distal-end cover member 72 has a distal-end opening 721 formed in the distal end thereof. As shown in FIG. 5, the distal-end opening 721 includes a central opening 721a in which the tip mounting part 5 is inserted in the assembled state, three semicircular openings (through holes) 721b which communicate with the central opening 721a and in which the pins 712 of the ejector member 71 are inserted, respectively, and a semicircular opening 721c in which an upper portion of the distal end of the holder 43 of the photometric unit 4 is inserted.

The case body 21 has, on its distal end face, a distal-end rib 725 extending along the outer peripheral edge of the central opening 721a except the openings 721b, 721c and projecting toward the distal end. In the tip mounted state, the proximal end (the flange 514) of the tip 500 abuts against the distal-end rib 725, thereby positioning the tip 500 with respect to the component measuring apparatus 1 (see FIG. 8(a), for example).

As shown in FIG. 6(b), the distal-end cover member 72 has through holes 722 formed respectively in opposite sides of the proximal end portion thereof, and the case body 21 has engaging portions 217 projecting outwardly respectively from opposite sides of the distal end portion thereof. As shown in FIG. 6(a), the distal-end cover member 72 has a receiving portion 723 on the inner surface of an upper portion thereof, and the case body 21 has a protrusion 218 projecting toward the distal end from an upper portion of the distal end thereof.

When the distal-end cover member 72 is mounted on the case 2 (the case body 21), the engaging portions 217 are inserted and fitted in the through holes 722, and the protrusion 218 is inserted in the receiving portion 723. In this manner, the distal-end cover member 72 is fixed to the case 2. In other words, the ejector mechanism 7 is fixed to the case 2. With this arrangement, the distal-end cover member 72 can be detached from the case 2 when necessary (e.g., when replacing the ejector mechanism 7).

As shown in FIG. 8, the distal-end cover member 72 has a step 724 on the inner surface of a lower portion thereof. The step 724 serves as a spring seat against which the distal end of the return spring 73 abuts. When the ejector mechanism 7 is assembled, as shown in FIG. 8, the return spring 73 has its distal end held in abutment against the step 724 and its proximal end held in abutment against the proximal end face of the recess 713 of the ejector member 71.

As shown in FIG. 8(a), when the tip 500 is mounted on the component measuring apparatus 1, the ejector member 71 of the ejector mechanism 7 is almost fully housed in the distal-end cover member 72. When the ejector member 71 is moved toward the distal end, as shown in FIG. 8(b), the pins 712 project from the distal-end cover member 72. The distal ends of the pins 712 abut against the proximal end (the flange 514) of the tip 500, pressing the tip 500 toward the distal end. Thus, the tip 500 is moved toward the distal end and removed (released) from the tip mounting part 5.

In the state shown in FIG. 8(b), the engaging portion 714 of the ejector member 71 engages with the engaging portion 216 of the case body 21, thereby preventing the ejector member 71 from moving toward the distal end. Therefore, the ejector mechanism 7 is prevented from being undesirably released from the case 2.

In the state (operational state) shown in FIG. 8(*b*), the return spring 73 is compressed, urging the ejector member 71 toward the proximal end. Therefore, when the finger hook 711 is released from the finger, the ejector member 71 is pushed toward the proximal end by the return spring 73 and moved into the state (initial state) shown in FIG. 8(*a*).

As shown in FIGS. 3 and 6, the case body 21, the lid 22, and the photometric unit 4 jointly define a space (housing space) 24 therebetween. In the space 24, the controller 10, the liquid crystal display device 6, and the cell mounting part (the recess 221) are housed. As described above, the O-ring 93 disposed between the case body 21 and the photometric unit 4 and the O-rings 91*a*, 91*b*, 92 disposed between the case body 21 and the lid 22 provide reliable hermetic sealing (liquid tightness, air tightness) in the space 24 (the case 2).

If blood (specimen) is adhered to the component measuring apparatus 1 at the time a blood glucose level (component) is measured, then since the case 2 is kept liquid-tight therein, the component measuring apparatus 1 can be washed with a cleaning solution and antisepticized with an antiseptic solution before a next blood glucose level (amount of glucose) is measured. If the case 2 is kept air-tight therein, then the component measuring apparatus 1 can be sterilized with an ethylene oxide gas (EOG) or the like in addition to being washed and antisepticized.

Therefore, even if the blood contains microorganisms harmful to the human body, which may include viruses such as HBV, HCV, HIV and pathogens, the operator is preferably prevented from being infected with such microorganisms.

Generally, it is difficult to keep hermetic sealing in areas where a moving member such as a lever or a slider is present. However, since the ejector mechanism 7 is disposed outside of the hermetically sealed space (the space 24), it is easy to keep hermetic sealing in the case 2.

<2nd Embodiment>

Next, a component measuring apparatus according to a second embodiment of the present invention will be described below.

Figure 10:
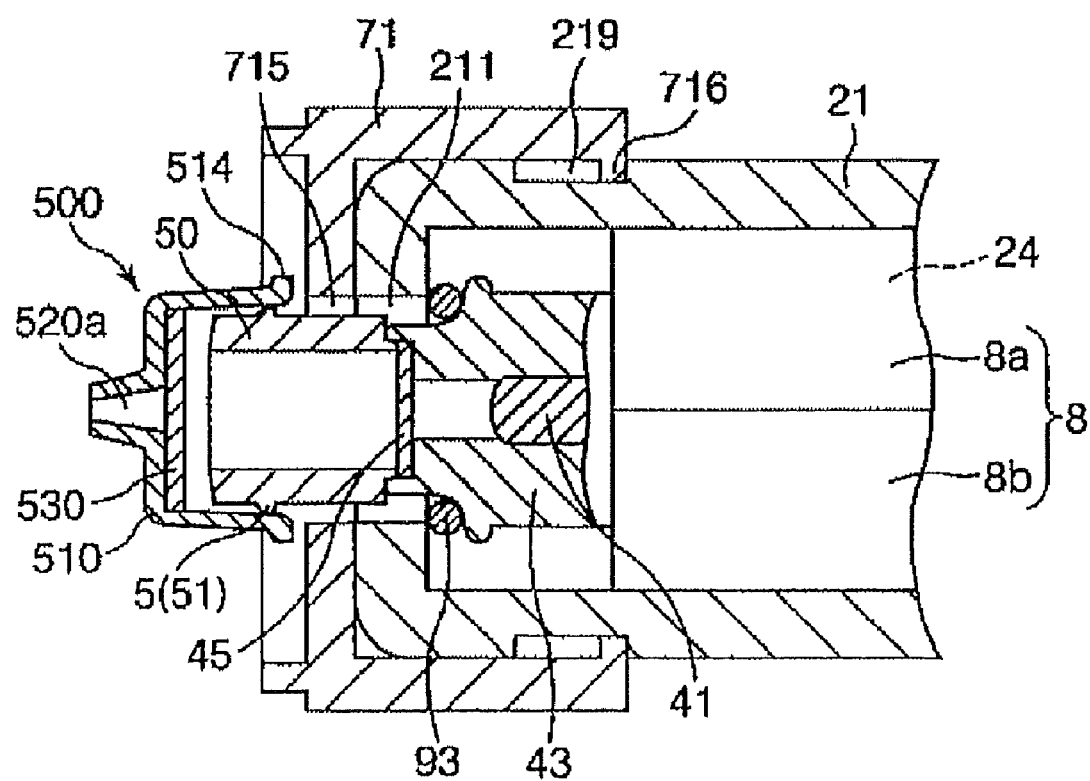
FIG. 10 is a vertical cross-sectional view showing structural details of a distal end portion of a component measuring apparatus according to a second embodiment of the present invention.

FIG. 10 is a vertical cross-sectional view showing structural details of a distal end portion of the component measuring apparatus according to the second embodiment of the present invention.

The component measuring apparatus according to the second embodiment will be described below. The differences between the component measuring apparatus according to the second embodiment and the component measuring apparatus according to the first embodiment will mainly be described below, and descriptions of identical details are omitted.

According to the second embodiment, the ejector mechanism 7 has different structural details, and the other details are identical to those of the first embodiment.

The ejector mechanism 7 shown in FIG. 10 is different from the ejector mechanism 7 according to the first embodiment in that the distal-end cover member 72 and the return spring 73 are omitted.

The ejector member 71 shown in FIG. 10 is in the form of a bottomed tube member and has a through hole 715 formed substantially centrally therein.

In the present embodiment, the photometric unit 4 is disposed in the case 2.

The tip mounting part 5 projects from the case 2 through the distal-end opening 211 and further projects from the distal end of the ejector member 71 through the through hole 715.

The ejector member 71 has a protrusion 716 projecting inwardly from the proximal end portion thereof, and the case body 21 has a recess 219 formed in a side surface of the distal end portion thereof at a position corresponding to the protrusion 716. When the ejector member 71 is mounted on the case 2, the protrusion 716 is inserted in the recess 219. Thereby, the ejector member 71 is movable along the axial directions of the case 2 and the movement of the ejector member 71 is also regulated.

For removing the tip 500 from the tip mounting part 5, the ejector member 71 is moved toward the distal end, and then, an edge defining the through hole 715 abuts against the proximal end (the flange 514) of the tip 500.

The second embodiment operates in the same manner and offers the same advantages as the first embodiment.

The structure according to the second embodiment is effective to reduce the number of parts of the ejector mechanism 7.

The ejector mechanism 7 may further have a cover (cap) detachably mounted on the distal end portion of the ejector member 71.

<3rd Embodiment>

Next, a component measuring apparatus according to a third embodiment of the present invention will be described below.

Figure 14:
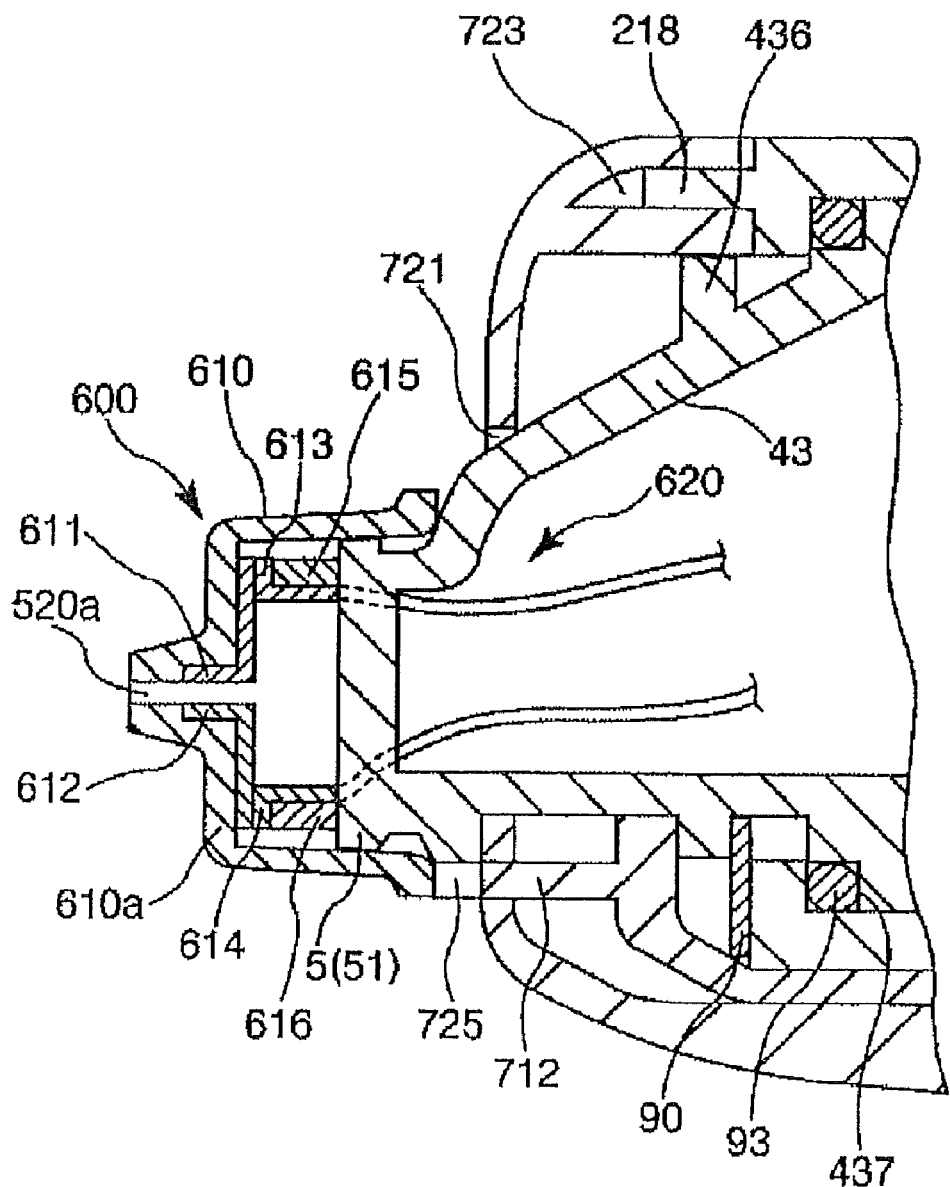
FIG. 14 is a vertical cross-sectional view showing structural details of a distal end portion of a component measuring apparatus according to a third embodiment of the present invention.

FIG. 14 is a vertical cross-sectional view showing structural details of a distal end portion of the component measuring apparatus according to the third embodiment of the present invention.

The component measuring apparatus according to the third embodiment will be described below. The differences between the component measuring apparatus according to the third embodiment and the component measuring apparatus according to the first embodiment will mainly be described below, and descriptions of identical details are omitted.

According to the third embodiment, the component measuring apparatus and the tip are of the electrode type, and the other details are identical to those of the first embodiment.

A tip 600 shown in FIG. 14 comprises a tip body 610 in the form of a bottomed tube, and a pair of electrodes (a measurement electrode 611 and a counter electrode 612) disposed on the bottom of the tip body 610.

The bottom 610*a* of the tip body 610 has a specimen introducing passage 520*a* formed therein for introducing a specimen of blood toward the measurement electrode 611 and the counter electrode 612. The specimen introducing passage 520*a* comprises a narrow tube and has an inner surface coated with a reactive reagent (e.g., glucose oxidase and potassium ferricyanide) which reacts with blood. The reagent coated is held in contact with the measurement electrode 611 and the counter electrode 612.

A detector 620 is disposed on the distal end portion of the holder 43. The detector 620 comprises electrode terminals 613, 614 electrically connected respectively to the measurement electrode 611 and the counter electrode 612 of the tip 600 in the tip mounted state, and terminal supports 615, 616 supporting the respective electrode terminals 613, 614 on the distal end portion of the holder 43.

With the component measuring apparatus 1 thus constituted, in the tip mounted state, the reagent reacts with the glucose of the blood that is introduced into the specimen introducing passage 520*a*, causing a current to flow between the measurement electrode 611 and the counter electrode 612. The component measuring apparatus 1 can detect a glucose level of the blood depending on the current.

The component measuring apparatus according to the present invention have been described above based on the embodiments. However, the present invention is not limited to the above embodiments.

In the above embodiments, blood has been described as the specimen. However, the specimen is not limited to blood, but may be a body fluid such as urine, lymphatic fluid, cerebrospinal fluid, saliva, or the like, or sewage such as factory effluent, household effluent, or the like, or its diluted solution or concentrated solution.

In the above embodiments, the glucose (glucose level) has been described as a target component (predetermined component) to be measured of the specimen (blood). However, the target component is not limited to the glucose, but may be cholesterol, uric acid, creatinine, lactic acid, hemoglobin (occult blood), any of various alcohols, any of various sugars, any of various proteins, any of various vitamins, any of various inorganic ions such as sodium, or an endocrine disruptor such as PCB, dioxin, or the like.

In the above embodiments, the level of a predetermined component is measured. According to the present invention, however, the quality of a predetermined component may be measured, or both the quantity and quality of a predetermined component may be measured.

In the above embodiments, each of the hermetic sealing means comprises an O-ring (a hermetic seal made of an elastic material). However, the hermetic sealing means may be of a material having a sealing capability (e.g., an adhesive) such as any of various resin materials.

In the first embodiment and the second embodiment, the component measuring apparatus which employ the mounted tubular tip with the test paper have been described. However, the component measuring apparatus according to the present invention may employ a chip in the form of a stick, a sheet, or the like.

Industrial Applicability:

A component measuring apparatus according to the present invention for measuring the quantity and/or quality of a predetermined component in a specimen, comprises a case including a tubular case body having a distal-end opening, a proximal-end opening, and a window, and a lid disposed so as to cover the proximal-end opening of the case body, a sampling device mounting part projecting outwardly from a distal end of the case body for detachably mounting thereon a sampling device for sampling the specimen, a detector for detecting the predetermined component, the detector being disposed in the distal-end opening of the case body and having at least a portion positioned inside the case body, a controller electrically connected to the detector and including a measuring unit for measuring the predetermined component, the controller having a function to control operation of at least the detector, a display having a function to display a measurement result measured by the measuring unit, for allowing the measurement result to be visually recognized through the window, a cell mounting part for mounting a cell for supplying electric power to at least the controller, first hermetic sealing means disposed in the distal-end opening between the case body and the detector, and second hermetic sealing means disposed in the proximal-end opening between the case body and the lid, wherein a housing space defined by the case body, the lid, and the detector for housing the controller, the display, and the cell mounting part is hermetically sealed by the first hermetic sealing means and the second hermetic sealing means. Therefore, the component measuring apparatus can be washed, antisepticized, or otherwise processed and can be used repeatedly with safety. The component measuring apparatus according to the present invention thus has industrial applicability.

The invention claimed is:

1. A component measuring apparatus for measuring a quantity and/or quality of a predetermined component in a specimen, comprising:
    a case including a tubular case body having a distal-end opening and a window formed in a side surface of the tubular case body;
    a detector for detecting the predetermined component, the detector being disposed in the distal-end opening of the case body and having at least a portion positioned inside the case body and a remaining portion projecting from the case body through the distal-end opening;
    a sampling device mounting part disposed on a distal-end portion of the detector and projecting outwardly from the detector for detachably mounting thereon a sampling device for sampling the specimen;
    a controller electrically connected to the detector to control operation of the detector, the controller being positioned in the tubular case body and including a measuring unit for measuring the predetermined component;
    a display operable to display a measurement result measured by the measuring unit, the display being positioned corresponding to the window to allow the measurement result displayed on the display to be visually observed through the window;
    a cell provided in the tubular case body for supplying electric power to at least the controller;
    hermetic sealing means disposed in the distal-end opening between the case and the detector for hermetically sealing; and
    an ejector member for removing the sampling device mounted on the sampling device mounting part from the sampling device mounting part, the ejector member being disposed outside of the detector and supported movably along axial directions of the case body.

2. A component measuring apparatus according to claim 1, wherein the case has an inner case in which is housed the controller and supporting at least the detector and the display.

3. A component measuring apparatus according to claim 1, wherein a distal-end cover member for guiding the ejector member for movement is disposed on the distal end portion of the case body.

4. A component measuring apparatus according to claim 3, wherein the ejector member has an abutment for abutting against the sampling device; and
    the distal-end cover member has a through hole in which is positioned the abutment.

5. A component measuring apparatus according to claim 3, wherein the distal-end cover member has a through hole in which is positioned at least the sampling device mounting part.

6. A component measuring apparatus according to claim 1, further comprising a switch electrically connected to the controller, and wherein the case body has a through hole in which is positioned a portion of the switch, the through hole being hermetically sealed by an elastic member.

7. A component measuring apparatus according to claim 6, wherein the elastic member is integrally formed with the case body by multicolor molding.

8. A component measuring apparatus according to claim 1, wherein the hermetic sealing means comprises an annular member disposed on an outer circumferential portion of the detector and made of an elastic material.

9. A component measuring apparatus according to claim 1, wherein the portion of the detector projecting from the case body has a projection projecting outwardly substantially perpendicularly to an axial direction of the case body, and further comprising a fitting member holding the hermetic sealing means in increased close contact with the case body and the detector, the fitting member being fitted between the projection and the distal end of the case body.

10. A component measuring apparatus according to claim 1, wherein the case body has an inspection through hole for inspecting the hermetic sealing of the component measuring apparatus, the inspection through hole being sealed by a sealing member.

11. A component measuring apparatus according to claim 10, wherein the inspection through hole is connectable to an inspecting device for inspecting the hermetic sealing of the component measuring apparatus.

* * * * *